United States Patent
Ono et al.

(10) Patent No.: US 11,255,020 B2
(45) Date of Patent: Feb. 22, 2022

(54) CARBON DIOXIDE ELECTROLYTIC SYSTEM

(71) Applicant: KABUSHIKI KAISHA TOSHIBA, Minato-ku (JP)

(72) Inventors: Akihiko Ono, Kita (JP); Yuki Kudo, Yokohama (JP); Ryota Kitagawa, Setagaya (JP); Masakazu Yamagiwa, Yokohama (JP); Jun Tamura, Chuo (JP); Satoshi Mikoshiba, Yamato (JP); Yoshitsune Sugano, Kawasaki (JP); Asahi Motoshige, Ota (JP); Takayuki Tsukagoshi, Kawasaki (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 176 days.

(21) Appl. No.: 16/560,669

(22) Filed: Sep. 4, 2019

(65) Prior Publication Data

US 2020/0002823 A1 Jan. 2, 2020

Related U.S. Application Data

(63) Continuation of application No. PCT/JP2018/033691, filed on Sep. 11, 2018.

(30) Foreign Application Priority Data

Mar. 20, 2018 (JP) .............................. JP2018-053472

(51) Int. Cl.
C25B 3/25 (2021.01)
C25B 1/04 (2021.01)
(Continued)

(52) U.S. Cl.
CPC .............. *C25B 3/25* (2021.01); *C07C 29/153* (2013.01); *C25B 1/04* (2013.01); *C25B 15/02* (2013.01); *C25B 15/08* (2013.01); *Y02E 60/36* (2013.01)

(58) Field of Classification Search
None
See application file for complete search history.

(56) References Cited

U.S. PATENT DOCUMENTS 9,157,158 B2 10/2015 Deguchi et al.
2008/0005964 A1* 1/2008 Hajiaghajani ........... C01B 3/501
48/61

(Continued)

FOREIGN PATENT DOCUMENTS

JP 3080865 B2 8/2000
JP 2001-246382 A 9/2001
(Continued)

OTHER PUBLICATIONS

Billy et al, Experimental Parameters Inlfuencing Hydrocarbon Selectivity during the Electrochemical Conversion of CO2, ACS Catalysis, vol. 7, No. 12, Nov. 2017, pp. 8467-8479 (Year: 2017).*

(Continued)

*Primary Examiner* — Harry D Wilkins, III
(74) *Attorney, Agent, or Firm* — Oblon, McClelland, Maier & Neustadt, L.L.P.

(57) ABSTRACT

A carbon dioxide reduction system comprises: an electrolytic unit including an electrolysis cell having a cathode to reduce a first substance containing carbon dioxide and thus produce a first product containing a carbon compound, and an anode to oxidize a second substance containing water or hydroxide ions and thus produce a second product containing oxygen, a detection unit to acquire data defining operation states of the electrolysis cell, and an electrolytic regulator to regulate electrolysis conditions of the electrolysis (Continued)

cell; a compression unit including a compressor to compress the first product, and a compressor regulator to regulate compression conditions of the first product by the compressor; and a controller programmed to predict a flow rate of the carbon compound discharged from the electrolysis cell in accordance with the data to control regulation of the compression conditions in accordance with the predicted flow rate.

11 Claims, 15 Drawing Sheets

(51) Int. Cl.
  *C25B 15/02* (2021.01)
  *C25B 15/08* (2006.01)
  *C07C 29/153* (2006.01)

(56) References Cited

U.S. PATENT DOCUMENTS

| | | | | |
|---|---|---|---|---|
| 2016/0017503 | A1* | 1/2016 | Kaczur | C25B 15/08 205/346 |
| 2016/0177459 | A1* | 6/2016 | Sato | C25B 11/051 204/230.2 |
| 2016/0369688 | A1* | 12/2016 | Hamad | C01B 3/12 |
| 2017/0067171 | A1* | 3/2017 | Ono | C25B 15/08 |
| 2017/0268118 | A1 | 9/2017 | Ono et al. | |
| 2018/0057950 | A1* | 3/2018 | Co | C25B 11/081 |
| 2018/0265440 | A1 | 9/2018 | Kudo et al. | |
| 2018/0274109 | A1 | 9/2018 | Kudo et al. | |
| 2019/0127865 | A1* | 5/2019 | Li | C25B 1/00 |

FOREIGN PATENT DOCUMENTS

| | | |
|---|---|---|
| JP | 2007-77464 A | 3/2007 |
| JP | 2013-119556 A | 6/2013 |
| JP | 2014-210982 A | 11/2014 |
| JP | 2017-172037 A | 9/2017 |
| JP | 2018-150595 A | 9/2018 |
| JP | 2018-154901 A | 10/2018 |

OTHER PUBLICATIONS

International Search Report dated Nov. 27, 2018 in PCT/JP2018/033691 filed Sep. 11, 2018 (with English Translation of Categories of Cited Documents).

Written Opinion dated Nov. 27, 2018 in PCT/JP2018/033691 filed Sep. 11, 2018.

Zengcai Liu, et al., "Electrochemical generation of syngas from water and carbon dioxide at industrially important rates", Journal of $CO_2$ Utilization, vol. 15, 2016, 7 pages.

Sichao Ma, et al., "Efficient Electrochemical Flow System with Improved Anode for the Conversion of $CO_2$ to CO", Journal of The Electrochemical SOciety, 161(10), 2014, pp. F1124-F1131.

* cited by examiner

FIG.5
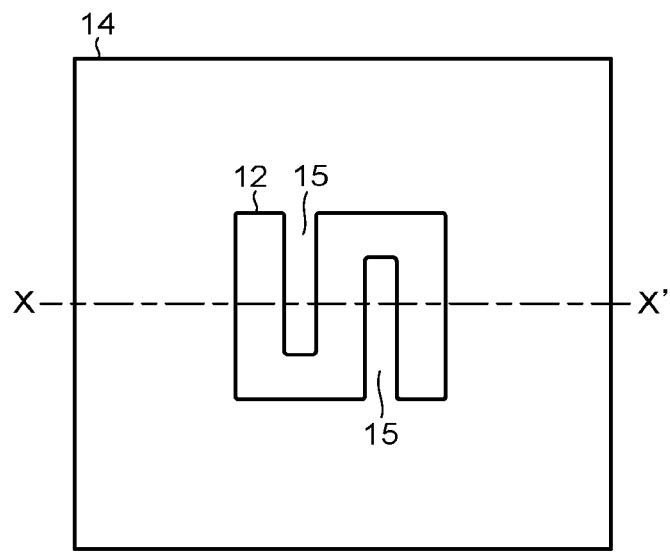
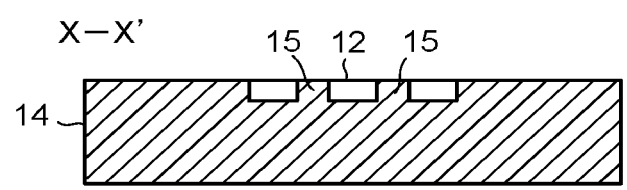
FIG.6
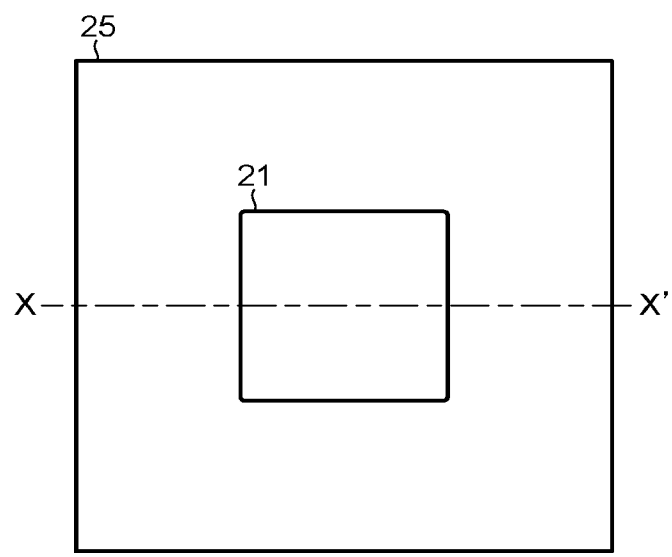
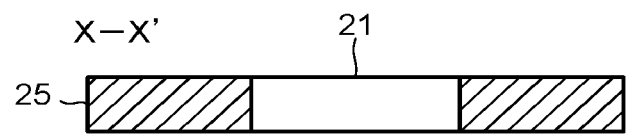

CARBON DIOXIDE ELECTROLYTIC SYSTEM

CROSS-REFERENCE TO RELATED APPLICATIONS

This application is a continuation of prior International Application No. PCT/JP2018/033691 filed on Sep. 11, 2018; the entire contents of all of which are incorporated herein by reference.

FIELD

Embodiments described herein relate to a carbon dioxide electrolytic system.

BACKGROUND

In recent years, depletion of fossil fuel such as petroleum or coal has been concerned, and expectation for sustainably-usable renewable energy has been rising. Examples of the renewable energy include a solar cell, wind power generation, and the like. Since a power production amount of these depends on weather and a natural situation, there is a problem that it is difficult to enable stable supply of electric power. For this reason, there has been made an attempt to store the electric power generated by the renewable energy in a storage battery, to thereby stabilize the electric power. However, when the electric power is stored, there are problems that a cost is required for the storage battery, and a loss occurs at a time of the storage.

With respect to such points, attention is focused on a technology in which water electrolysis is performed by using the electric power generated by the renewable energy to produce hydrogen ($H_2$) from water, or carbon dioxide ($CO_2$) is electrochemically reduced to be converted into a chemical substance (chemical energy) such as a carbon compound such as carbon monoxide (CO), formic acid (HCOOH), methanol ($CH_3OH$), methane ($CH_4$), acetic acid ($CH_3COOH$), ethanol ($C_2H_5OH$), ethane ($C_2H_6$), or ethylene ($C_2H_4$). When these chemical substances are stored in a cylinder or a tank, there are advantageous points that a storage cost of energy can be reduced, and a storage loss is also small when compared to a case where the electric power (electric energy) is stored in the storage battery.

As a carbon dioxide electrolytic device, for example, there has been studied a structure in which an Ag nanoparticle catalyst is used as a cathode, a cathode solution and $CO_2$ gas are brought into contact with the cathode, and an anode solution is brought into contact with an anode. An example of a concrete configuration of the electrolytic device includes, for example, a configuration which includes a cathode solution flow path disposed along one surface of the cathode, a $CO_2$ gas flow path disposed along the other surface of the cathode, an anode solution flow path disposed along one surface of an anode, and a separator disposed between the cathode solution flow path and the anode solution flow path.

BRIEF DESCRIPTION OF THE DRAWINGS

FIG. 5 is a view illustrating an example of an anode solution flow path in the electrolysis cell.
FIG. 6 is a view illustrating an example of a cathode solution flow path in the electrolysis cell.

DETAILED DESCRIPTION

A carbon dioxide reduction system of an embodiment comprises: an electrolytic unit including an electrolysis cell having a cathode to reduce a first substance containing carbon dioxide and thus produce a first product containing a carbon compound, and an anode to oxidize a second substance containing water or hydroxide ions and thus produce a second product containing oxygen, a detection unit to acquire data defining operation states of the electrolysis cell, and an electrolytic regulator to regulate electrolysis conditions of the electrolysis cell; a compression unit including a compressor to compress the first product, and a compressor regulator to regulate compression conditions of the first product by the compressor; and a controller programmed to predict a flow rate of the carbon compound discharged from the electrolysis cell in accordance with the data to control regulation of the compression conditions in accordance with the predicted flow rate.

Hereinafter, a carbon dioxide electrolytic device according to an embodiment will be described with reference to the drawings. In each embodiment presented below, substantially the same components are denoted by the same reference signs, and a description thereof is sometimes partially omitted. The drawings are schematic, and a relationship between a thickness and a planar size, thickness proportions of the respective portions, and the like are sometimes different from actual ones.

Figure 1:
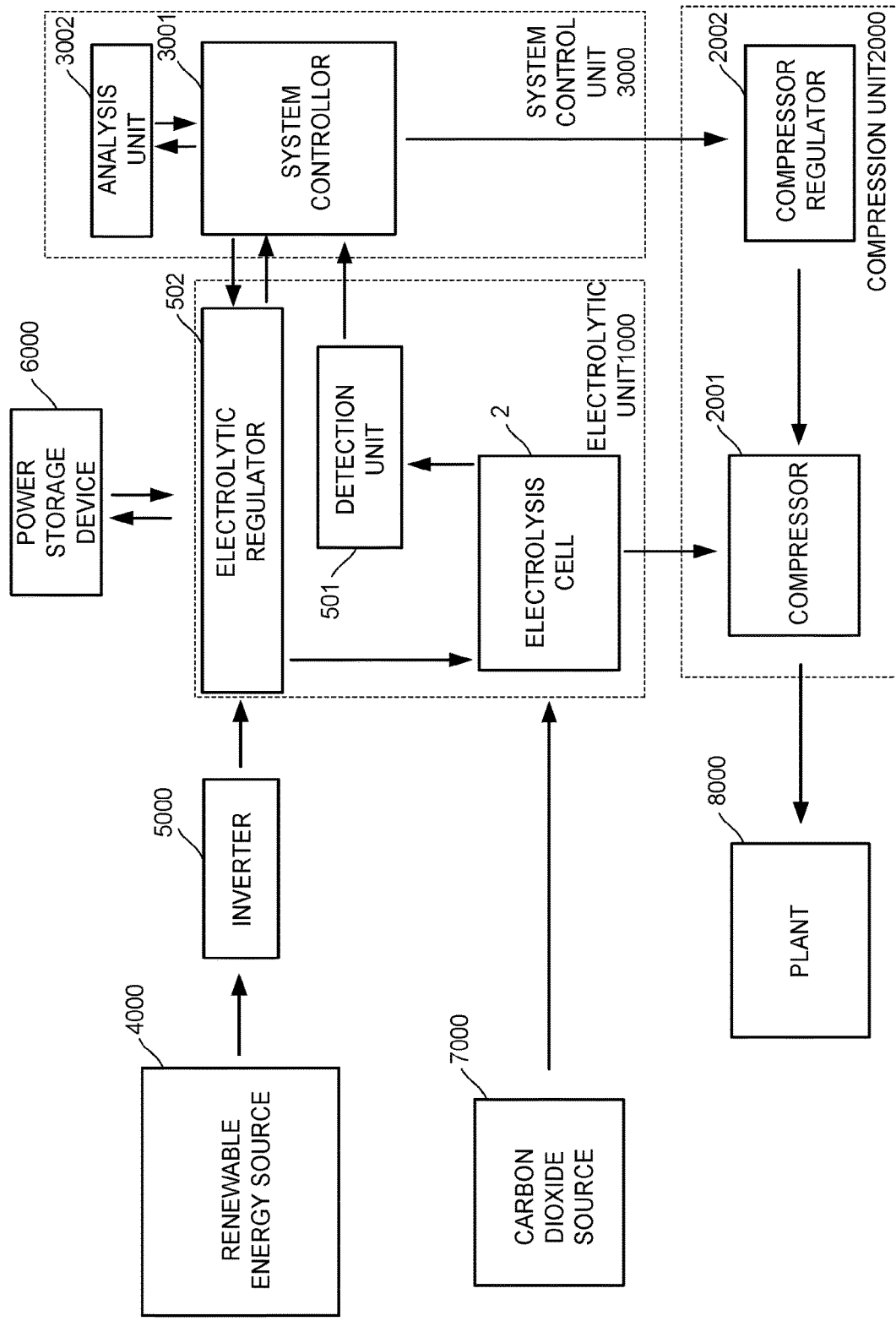
FIG. 1 is a view illustrating a configuration example of an electrolytic system.

FIG. 1 is a view illustrating a configuration example of a carbon dioxide electrolytic system according to an embodiment. FIG. 1 illustrates an electrolytic unit 1000, a compression unit 2000, a system controller 3000, a renewable energy source 4000, an inverter 5000, a power storage device 6000, a carbon dioxide source 7000, and a plant 8000.

The electrolytic unit 1000 includes an electrolysis cell 2 which produces a reduction product containing a carbon compound such as carbon monoxide by reducing a substance such as carbon dioxide. An amount of the carbon compound produced by the electrolysis cell 2 changes in accordance with operation states of the electrolysis cell 2.

The electrolysis cell 2 is driven by electric energy supplied from the renewable energy source 4000 such as, for example, a solar cell or wind power generator through the inverter 5000. Since the renewable energy is unstable, an amount of the electric energy constantly changes. Excessive electric energy is charged into the power storage device 6000 such as a battery and supplied to the electrolysis cell 2 when it is necessary. The electrolysis cell 2 performs an electrolysis operation by using carbon dioxide supplied from the carbon dioxide source 7000 such as, for example, a power station. An amount of carbon dioxide produced at the carbon dioxide source 7000 changes. As mentioned above, since the amount of the electric energy and the amount of carbon dioxide supplied to the electrolysis cell 2 are unstable, it is difficult to perform the stable electrolysis operation in the electrolysis cell 2.

The reduction product is supplied from the electrolytic unit 1000 to the compression unit 2000. The compression unit 2000 includes a compressor 2001 compressing the reduction product and a compressor regulator 2002 regulating compression conditions of the reduction product by the compressor 2001. The compressor 2001 has, for example, a tank to accommodate the compressed reduction product. The reduction product is compressed by the compressor 2001 and stored in a storage tank of the plant 8000 such as a chemical plant.

When the electrolysis operation by the electrolysis cell 2 is unstable as mentioned above, an amount of a produced carbon compound is also unstable. At this time, the compression conditions of the reduction product used by the compressor 2001 are preferably controlled in accordance with the amount of the reduction product by the compressor regulator 2002.

In the electrolytic system of the embodiment, one or more types of data defining operation states of the electrolysis cell 2 are acquired by a detection unit 501 including one or more types of sensors, a flow rate of a specific reduction product is predicted based on the data by the system controller 3000 including a system control device 3001 and an analysis unit 3002, and at least one of an electrolytic regulator 502 and the compressor regulator 2002 is controlled in accordance with the predicted flow rate. It is possible to stably operate the electrolysis cell 2 and the compressor 2001 in accordance with the production amount of the reduction product by feeding back the operation states of the electrolysis cell 2 to the electrolytic regulator 502 and the compressor regulator 2002 to control the regulation of the electrolysis conditions by the electrolytic regulator 502 and the regulation of the compression conditions of the reduction product by the compressor regulator 2002. It is thereby possible to suppress an effect due to a change in the operation states of the electrolysis cell 2 on, for example, the compressor 2001 and an entire system.

The electrolytic regulator 502, the compressor regulator 2002, the system control device 3001, and the analysis unit 3002 may be configured by using hardware using, for example, a processor, or the like. Each operation may be stored in a computer readable recording medium such as a memory as an operation program, and each operation may be executed by appropriately reading the operation program stored in the recording medium by the hardware.

Figure 2:
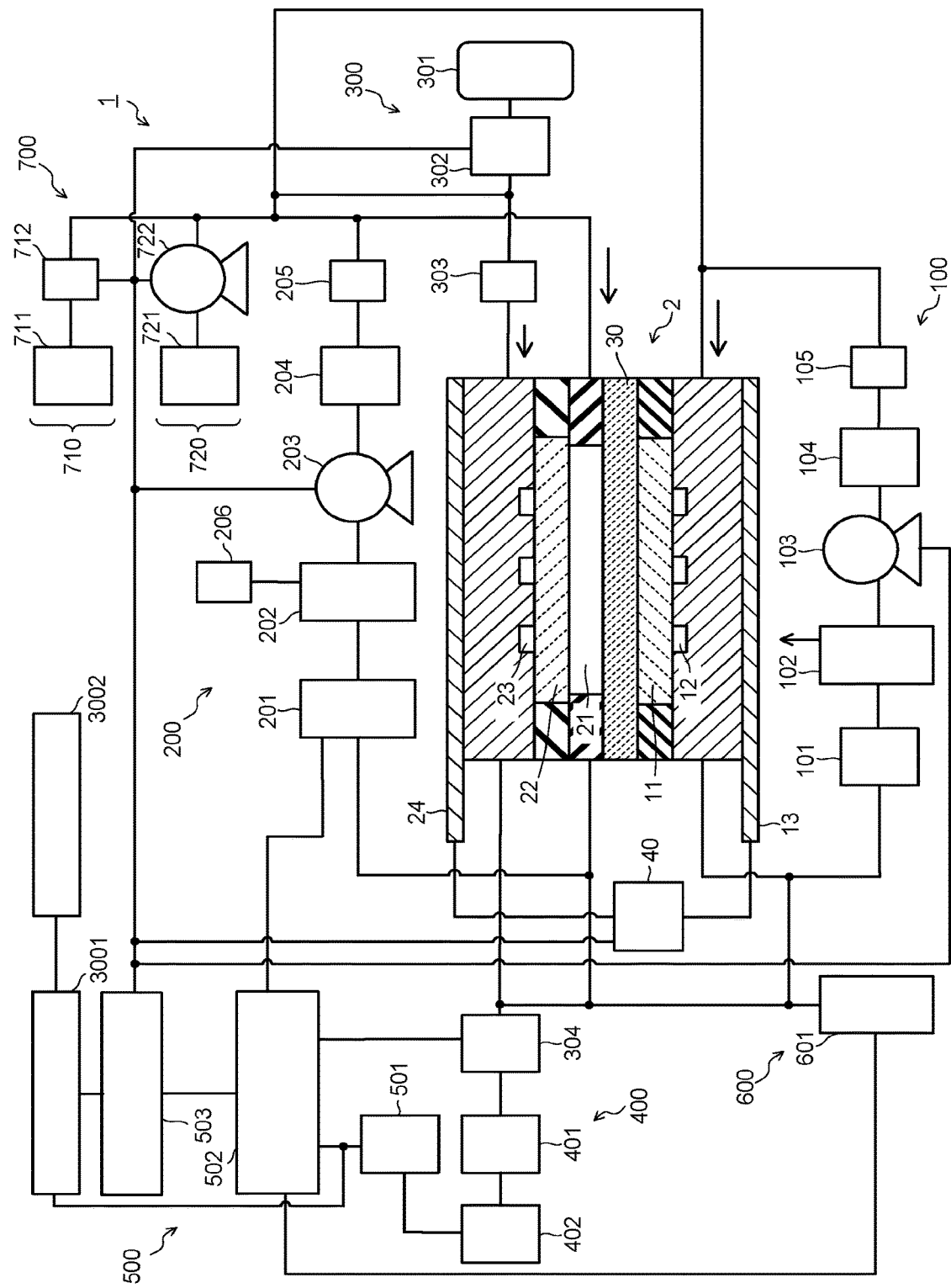
FIG. 2 is a view illustrating a configuration example of an electrolytic device.
Figure 3:
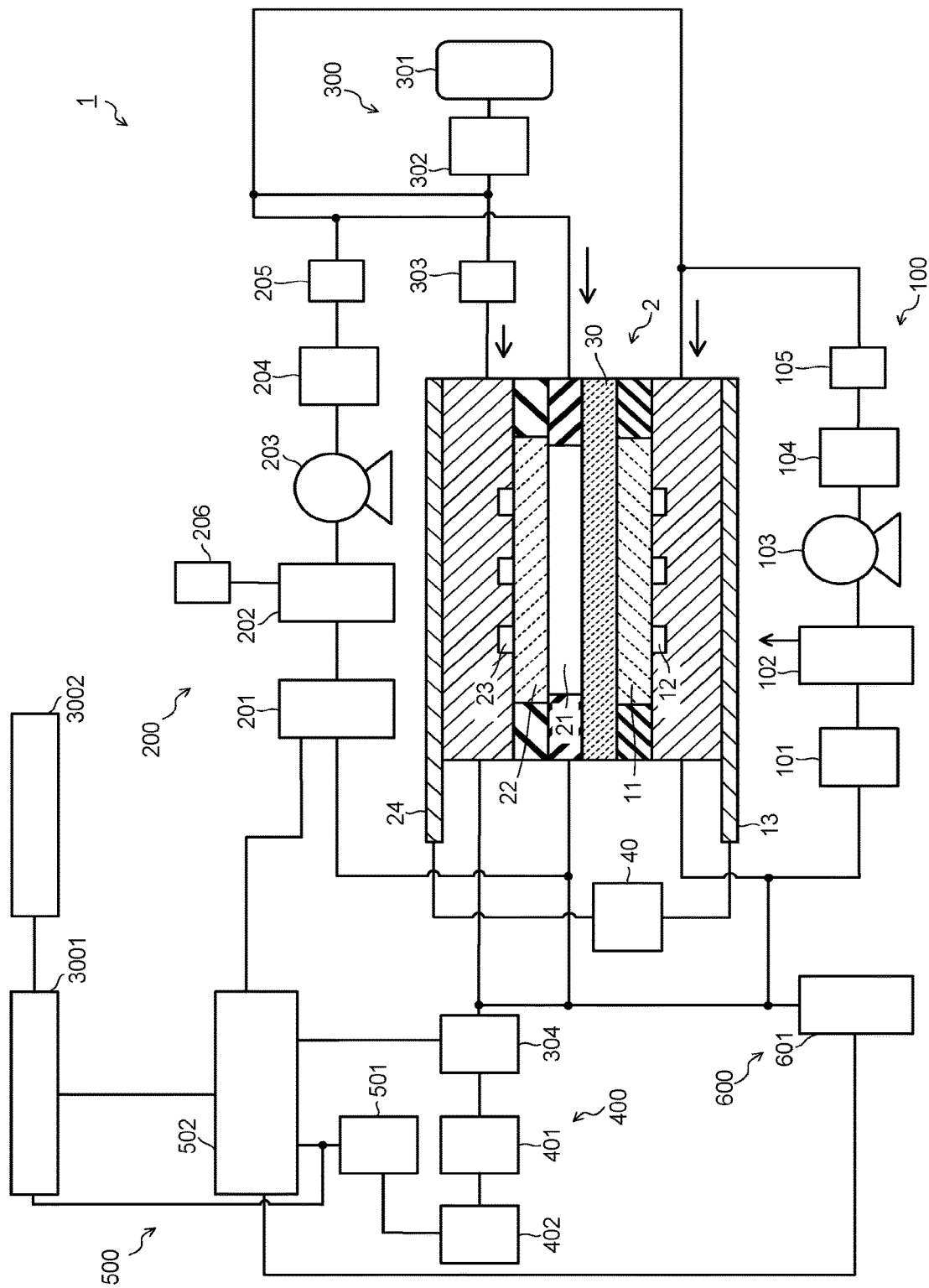
FIG. 3 is a view illustrating another configuration example of the electrolytic device.
Figure 4:
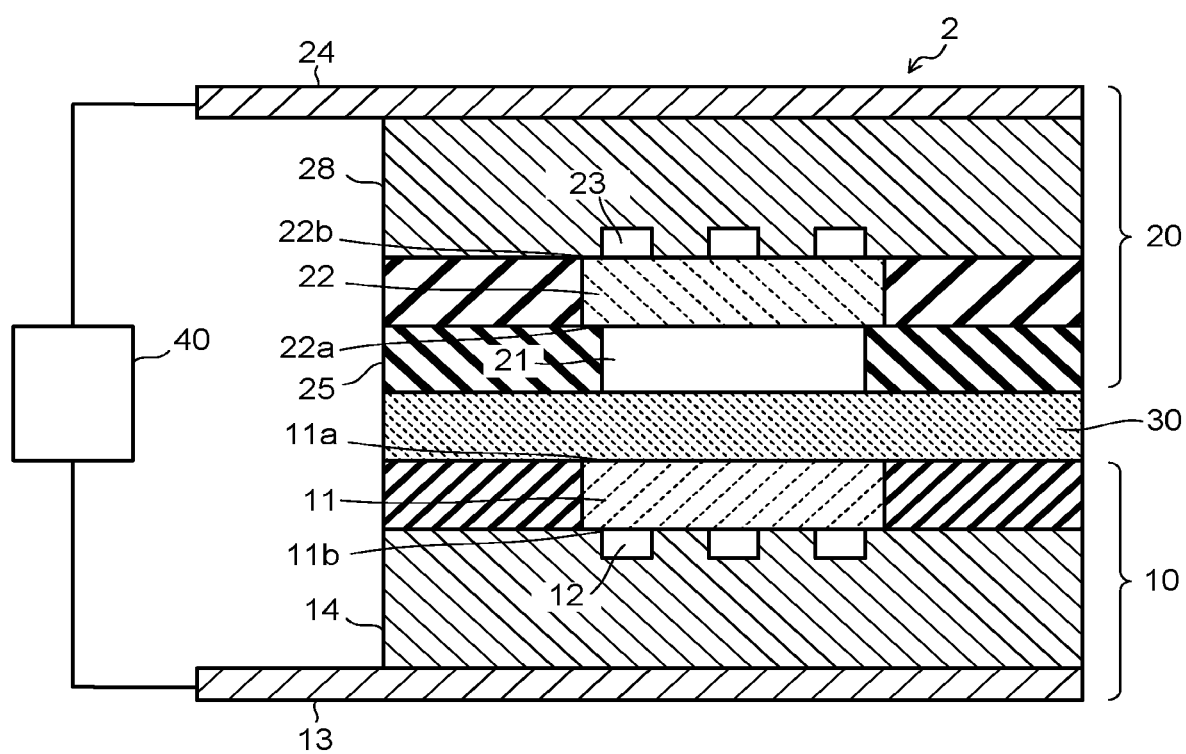
FIG. 4 is a sectional view illustrating a configuration example of an electrolysis cell.

The configuration example of the electrolytic unit 1000 is further explained with reference to FIG. 2 to FIG. 4. FIG. 2 is a view illustrating a configuration example of an electrolytic device forming the electrolytic unit 1000, FIG. 3 is a view illustrating another configuration example of the electrolytic device, and FIG. 4 is a sectional view illustrating a configuration of an electrolysis cell in the electrolytic device. A carbon dioxide electrolytic device 1 illustrated in FIG. 2 and FIG. 3 includes: the electrolysis cell 2, an anode solution supply system 100 which supplies an anode solution to the electrolysis cell 2; a cathode solution supply system 200 which supplies a cathode solution to the electrolysis cell 2; a gas supply system 300 which supplies carbon dioxide ($CO_2$) gas to the electrolysis cell 2; a product collection system 400 which collects a product produced by a reduction reaction in the electrolysis cell 2; a control system 500 which detects a type and a production amount of the collected product, and performs control of the product and control of a refresh operation; a waste solution collection system 600 which collects a waste solution of the cathode solution and the anode solution, and a refresh material source 700 which recovers an anode, a cathode, or the like of the electrolysis cell 2. Note that the refresh material source 700 is not necessarily provided as illustrated in FIG. 3.

The electrolysis cell 2 includes an anode part 10, a cathode part 20, and a separator 30. The anode part 10 includes an anode 11, an anode solution flow path 12, and an anode current collector 13. The cathode part 20 includes a cathode solution flow path 21, a cathode 22, a $CO_2$ gas flow path 23, and a cathode current collector 24. It is preferable if the separator 30 and the cathode 22 are in contact without being provided with the cathode solution flow path 21 because a cell resistance becomes low. The separator 30 is disposed to separate the anode part 10 and the cathode part 20. The electrolysis cell 2 is sandwiched by a pair of non-illustrated support plates, and further tightened with bolts or the like. In FIG. 2 and FIG. 3, there is provided a power controller 40 which makes a current flow through the anode 11 and the cathode 22. The power controller 40 is connected to the anode 11 and the cathode 22 through a current introduction member. The power controller 40 is not limited to a normal system power supply, battery, or the like, and may have a power source which supplies electric power generated by the renewable energy source 4000 such as a solar cell or wind power generation. Note that the power controller 40 may also have the aforementioned power source and a power controller or the like which adjusts output of the aforementioned power source to control a voltage between the anode 11 and the cathode 22.

The anode 11 is an electrode (oxidation electrode) which causes an oxidation reaction of water ($H_2O$) in an anode solution as an electrolytic solution to produce oxygen ($O_2$) or hydrogen ions ($H^+$), or causes an oxidation reaction of hydroxide ions ($OH^-$) produced at the cathode part 20 to produce oxygen ($O_2$) or water ($H_2O$). The anode 11 preferably has a first surface 11a which is in contact with the separator 30, and a second surface 11b which faces the anode solution flow path 12. The first surface 11a of the anode 11 is brought into close contact with the separator 30. The anode solution flow path 12 is to supply the anode solution to the anode 11, and is formed of a pit (groove portion/depression) provided at a flow path plate 14. The anode solution flows through inside the anode solution flow path 12 so as to be in contact with the anode 11. The anode current collector 13 is electrically in contact with a surface on a side opposite to the anode 11 of the first flow path plate 14 which forms the anode solution flow path 12.

As described above, in the electrolysis cell 2 of the embodiment, the anode 11 and the separator 30 are brought into close contact with each other. Oxygen ($O_2$) is produced in the anode 11, and at this time, in a cell structure in which the separator 30 is sandwiched by the cathode solution flow path and the anode solution flow path, air bubbles of oxygen ($O_2$) gas generated in the anode 11 stay in the anode solution flow path, and a cell resistance between the anode 11 and the separator (ion-exchange membrane or the like) increases, this sometimes increases a voltage variation of the anode 11. With respect to a point as above, oxygen gas generated at the anode 11 is discharged to the anode solution flow path 12 together with the anode solution by bringing the anode 11 and the separator 30 into close contact with each other without providing the anode solution flow path 12 between the anode 11 and the separator 30. This makes it possible to prevent the oxygen gas from staying between the anode 11 and the separator 30, and to suppress a variation in a cell voltage due to the voltage variation of the anode 11.

Non-illustrated solution inlet port and solution outlet port are provided at the first flow path plate 14, and the anode solution is introduced and discharged by the anode solution supply system 100 through these solution inlet port and solution outlet port. A material having low chemical reactivity and high conductivity is preferably used for the first flow path plate 14. Examples of such a material include a metal material such as Ti or SUS, carbon, or the like. A plurality of lands (protrusions) 15 are preferably provided along the anode solution flow path 12, as illustrated in FIG. 5. The lands 15 are provided for mechanical retention and electrical continuity. The lands 15 are preferably provided alternately to uniformize flow of the anode solution. The above lands 15 make the anode solution flow path 12 serpentine. Moreover, the lands 15 are preferably provided alternately along the anode solution flow path 12 to make the anode solution flow path 12 serpentine also to enable smooth discharging of the anode solution in which oxygen ($O_2$) gas is mixed.

The anode 11 is preferably mainly formed by a catalyst material (anode catalyst material) capable of oxidizing water ($H_2O$) to produce oxygen or hydrogen ions or oxidizing hydroxide ions ($OH^-$) to produce water or oxygen, and capable of reducing an overvoltage of the above reaction. Examples of such a catalyst material include a metal such as platinum (Pt), palladium (Pd), or nickel (Ni), an alloy or an intermetallic compound containing the above metals, a binary metal oxide such as a manganese oxide (Mn—O), an iridium oxide (Ir—O), a nickel oxide (Ni—O), a cobalt oxide (Co—O), an iron oxide (Fe—O), a tin oxide (Sn—O), an indium oxide (In—O), a ruthenium oxide (Ru—O), a lithium oxide (Li—O), or a lanthanum oxide (La—O), a ternary metal oxide such as Ni—Co—O, Ni—Fe—O, La—Co—O, Ni—La—O, or Sr—Fe—O, a quaternary metal oxide such as Pb—Ru—Ir—O or La—Sr—Co—O, or a metal complex such as a Ru complex or a Fe complex.

The anode 11 includes a base material having a structure capable of moving the anode solution or ions between the separator 30 and the anode solution flow path 12, for example, a porous structure such as a mesh material, a punching material, a porous body, or a metal fiber sintered body. The base material may be formed by a metal such as titanium (Ti), nickel (Ni), or iron (Fe), or a metal material such as an alloy (for example, SUS) containing at least one of these metals, or may be formed by the above-described anode catalyst material. When the oxide is used as the anode catalyst material, a catalyst layer is preferably formed by adhering or stacking the anode catalyst material on a surface of the base material formed by the above-described metal material. The anode catalyst material preferably has nanoparticles, a nanostructure, a nanowire, or the like for the purpose of increasing the oxidation reaction. The nanostructure is a structure in which nanoscale irregularities are formed on a surface of the catalyst material.

The cathode 22 is an electrode (reduction electrode) which causes a reduction reaction of carbon dioxide ($CO_2$) or a reduction reaction of a carbon compound produced thereby to produce a carbon compound such as carbon monoxide (CO), methane ($CH_4$), ethane ($C_2H_6$), ethylene ($C_2H_4$), methanol ($CH_3OH$), ethanol ($C_2H_5OH$), or ethylene glycol ($C_2H_6O_2$). In the cathode 22, a side reaction in which hydrogen ($H_2$) is produced by a reduction reaction of water ($H_2O$) is sometimes caused simultaneously with the reduction reaction of carbon dioxide ($CO_2$). The cathode 22 has a first surface 22a facing the cathode solution flow path 21 and a second surface 22b facing the $CO_2$ gas flow path 23. The cathode solution flow path 21 is disposed between the cathode 22 and the separator 30 so that the cathode solution as an electrolytic solution is in contact with the cathode 22 and the separator 30.

The cathode solution flow path 21 is formed by an opening portion provided at a second flow path plate 25. Non-illustrated solution inlet port and solution outlet port are provided at the second flow path plate 25, and the cathode solution is introduced and discharged by the cathode solution supply system 200 through these solution inlet port and solution outlet port. The cathode solution flows through in the cathode solution flow path 21 so as to be in contact with the cathode 22 and the separator 30. A material having low chemical reactivity and having no conductivity is preferably used for the second flow path plate 25 forming the cathode solution flow path 21. Examples of such a material include an insulating resin material such as an acrylic resin, polyetheretherketone (PEEK), or a fluorocarbon resin.

Figure 7:
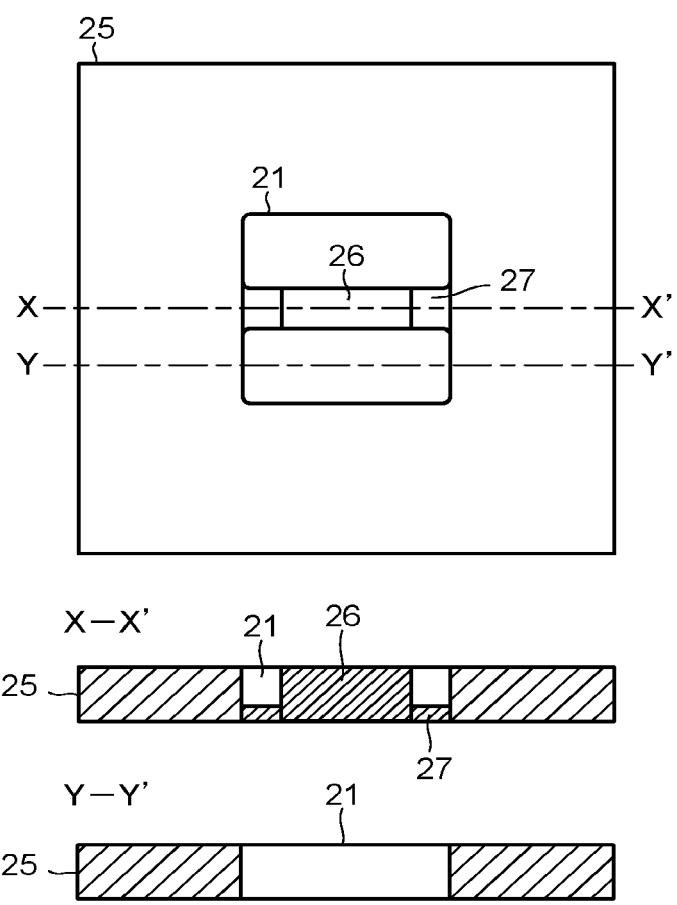
FIG. 7 is a view illustrating another example of the cathode solution flow path in the electrolysis cell.

In the cathode 22, the reduction reaction of $CO_2$ occurs mainly at a part in contact with the cathode solution. Accordingly, as illustrated in FIG. 6, the opening portion having a large opening area is preferably applied to the cathode solution flow path 21. However, a land (protrusion) 26 may be provided at the cathode solution flow path 21 in order to enhance mechanical retention and electrical connectivity, as illustrated in FIG. 7. The land 26 at the cathode solution flow path 21 is provided at a center portion of the cathode solution flow path 21, and is retained to the second flow path plate 25 by a bridge portion 27 thinner than the land 26 so as not to prevent the cathode solution in the cathode solution flow path 21 from flowing through. When the land 26 is provided at the cathode solution flow path 21, the number of lands 26 is preferably small in order to reduce cell resistance.

The $CO_2$ gas flow path 23 is formed by a pit (groove portion/depression) provided at a third flow path plate 28. A material having low chemical reactivity and high conductivity is preferably used for the third flow path plate 28 forming the $CO_2$ gas flow path. Examples of such a material include the metal material such as Ti or SUS, carbon, or the like. Note that non-illustrated inlet port and outlet port for a solution or gas, screw holes for tightening, and the like are provided at each of the first flow path plate 14, the second flow path plate 25, and the third flow path plate 28. Further, a non-illustrated packing is sandwiched in front of and behind each of the flow path plates 14, 25, and 28 as necessary.

Figure 8:
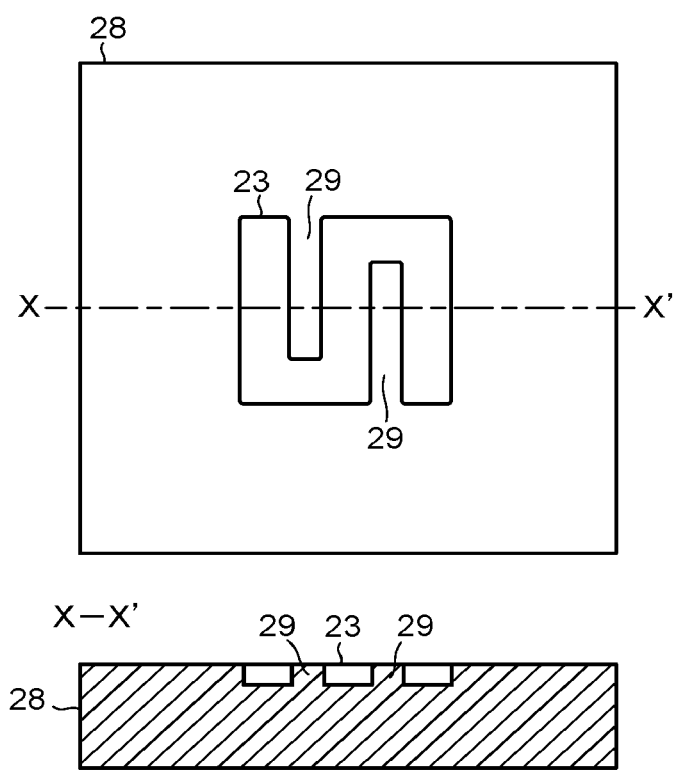
FIG. 8 is a view illustrating an example of a $CO_2$ gas flow path in the electrolysis cell.

Non-illustrated gas inlet port and gas outlet port are provided at the third flow path plate 28, and $CO_2$ gas or gas containing $CO_2$ (sometimes collectively referred to simply as $CO_2$ gas) is introduced and discharged by the gas supply system 300 through these gas inlet port and gas outlet port. The $CO_2$ gas flows through in the $CO_2$ gas flow path 23 so as to be in contact with the cathode 22. A plurality of lands (protrusions) 29 are preferably provided along the $CO_2$ gas flow path 23, as illustrated in FIG. 8. The lands 29 are provided for the mechanical retention and the electrical continuity. The lands 29 are preferably provided alternately, and this makes the $CO_2$ gas flow path 23 serpentine similarly to the anode solution flow path 12. The cathode current collector 24 is electrically in contact with a surface on a side opposite to the cathode 22 of the third flow path plate 28.

In the electrolysis cell 2 of the embodiment, providing the lands 15 and the lands 29 along the anode solution flow path 12 and the $CO_2$ gas flow path 23 makes it possible to increase a contact area between the anode 11 and the first flow path plate 14 forming the anode solution flow path 12 and a contact area between the cathode 22 and the third flow path plate 28 forming the $CO_2$ gas flow path 23. Further, providing the land 26 at the cathode solution flow path 21 makes it possible to increase a contact area between the cathode 22 and the second flow path plate 25 forming the cathode solution flow path 21. These make electrical continuity between the anode current collector 13 and the cathode current collector 24 good while enhancing mechanical retentivity of the electrolysis cell 2, and make it possible to improve reduction reaction efficiency of $CO_2$, or the like.

Figure 9:
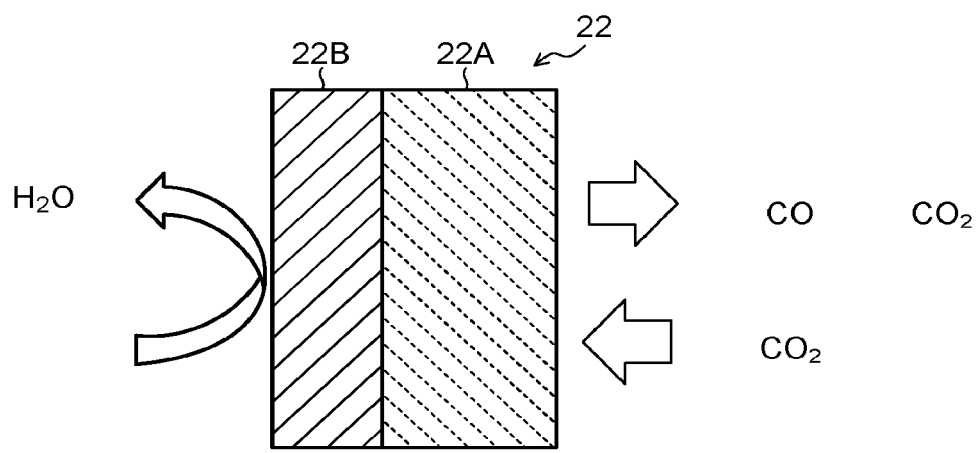
FIG. 9 is a view illustrating an example of a cathode in the electrolysis cell.
Figure 10:
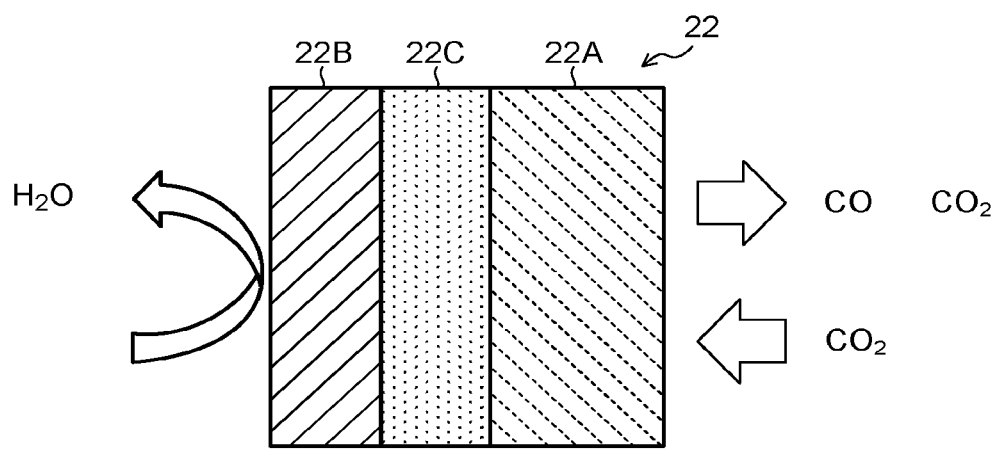
FIG. 10 is a view illustrating another example of the cathode in the electrolysis cell.
Figure 11:
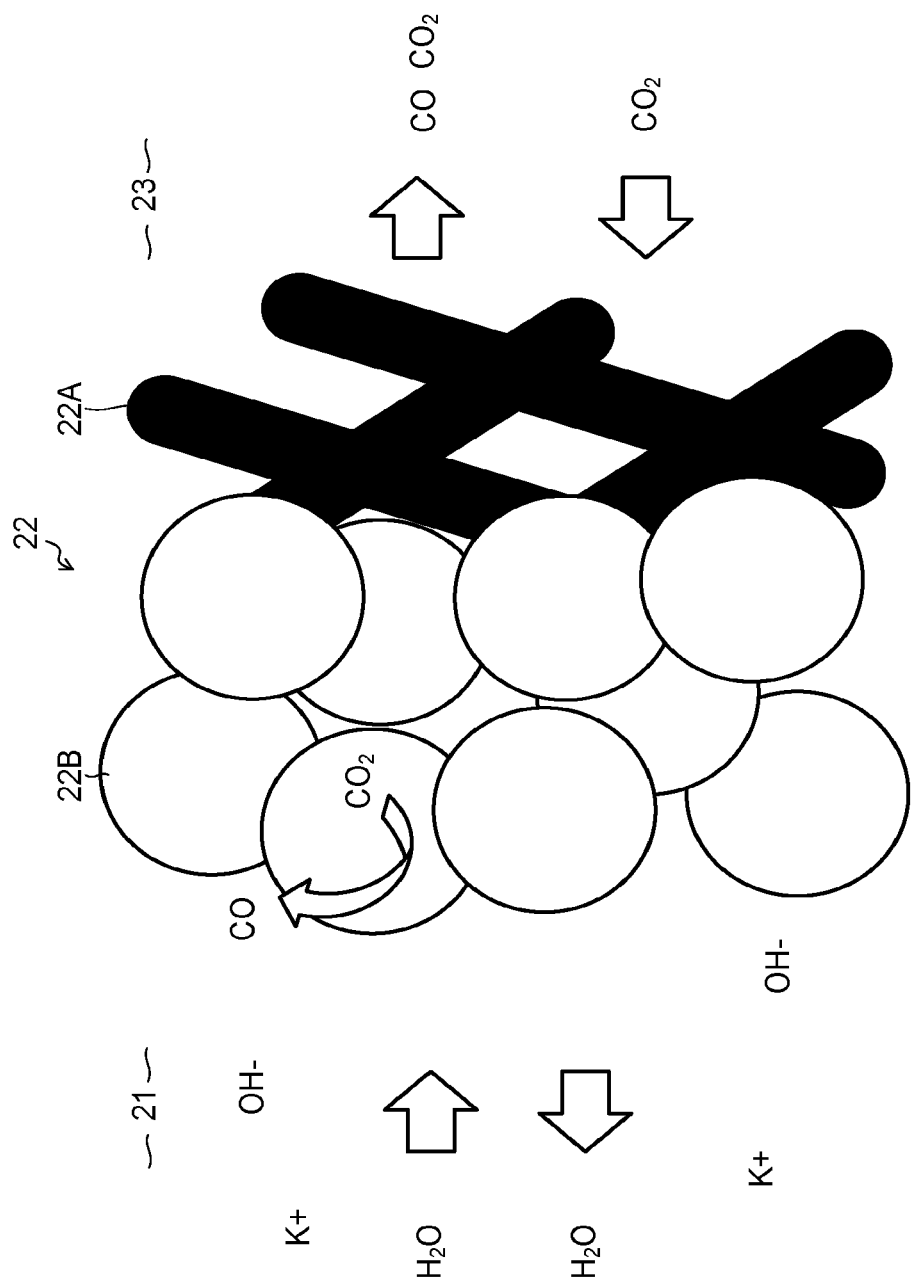
FIG. 11 is a view schematically illustrating a reaction in the cathode in the electrolysis cell.

As illustrated in FIG. 9, the cathode 22 has a gas diffusion layer 22A and a cathode catalyst layer 22B provided on the gas diffusion layer 22A. As illustrated in FIG. 10, a porous layer 22C denser than the gas diffusion layer 22A may be disposed between the gas diffusion layer 22A and the cathode catalyst layer 22B. As illustrated in FIG. 11, the gas diffusion layer 22A is disposed on the $CO_2$ gas flow path 23 side, and the cathode catalyst layer 22B is disposed on the cathode solution flow path 21 side. The cathode catalyst layer 22B may enter the gas diffusion layer 22A. The cathode catalyst layer 22B preferably has catalyst nanoparticles, a catalyst nanostructure, or the like. The gas diffusion layer 22A is formed by, for example, carbon paper, carbon cloth, or the like, and water repellent treatment is performed thereon. The porous layer 22C is formed by a porous body whose pore size is smaller than that of the carbon paper or the carbon cloth.

As illustrated in a schematic view in FIG. 11, the cathode solution or ions are supplied and discharged from the cathode solution flow path 21 at the cathode catalyst layer 22B. In the gas diffusion layer 22A, the $CO_2$ gas is supplied from the $CO_2$ gas flow path 23, and a product obtained by the reduction reaction of the $CO_2$ gas is discharged. By previously performing moderate water repellent treatment on the gas diffusion layer 22A, the $CO_2$ gas reaches the cathode catalyst layer 22B mainly through gas diffusion. The reduction reaction of $CO_2$ or the reduction reaction of a carbon compound produced thereby occurs in the vicinity of a boundary between the gas diffusion layer 22A and the cathode catalyst layer 22B or in the vicinity of the cathode catalyst layer 22B which enters the gas diffusion layer 22A, a gaseous product is discharged mainly from the $CO_2$ gas flow path 23, and a liquid product is discharged mainly from the cathode solution flow path 21.

The cathode catalyst layer 22B is preferably formed by a catalyst material (cathode catalyst material) capable of reducing carbon dioxide and water to produce a carbon compound and hydrogen, capable of reducing the carbon compound produced thereby to produce a carbon compound according to need, and capable of decreasing overvoltage in the above reaction. Examples of such a material include a metal such as gold (Au), silver (Ag), copper (Cu), platinum (Pt), palladium (Pd), nickel (Ni), cobalt (Co), iron (Fe), manganese (Mn), titanium (Ti), cadmium (Cd), zinc (Zn), indium (In), gallium (Ga), lead (Pb), or tin (Sn), a metal material such as an alloy or an intermetallic compound containing at least one of the above metals, a carbon material such as carbon (C), graphene, CNT (carbon nanotube), fullerene, or ketjen black, or a metal complex such as a Ru complex or a Re complex. The cathode catalyst layer 22B can employ various shapes such as a plate shape, a mesh shape, a wire shape, a particle shape, a porous shape, a thin film shape, and an island shape.

The cathode catalyst material forming the cathode catalyst layer 22B preferably has nanoparticles of the above-described metal material, a nanostructure of the metal material, a nanowire of the metal material, or a composite body in which the nanoparticles of the above-described metal material are supported by a carbon material such as carbon particles, a carbon nanotube, or graphene. By applying catalyst nanoparticles, a catalyst nanostructure, a catalyst nanowire, a catalyst nano-support structure, or the like as the cathode catalyst material, it is possible to increase reaction efficiency of the reduction reaction of carbon dioxide at the cathode 22.

The separator 30 is formed by an ion exchange membrane or the like capable of making ions move between the anode 11 and the cathode 22, and separating the anode part 10 and the cathode part 20. As the ion exchange membrane, it is possible to use, for example, a cation exchange membrane such as Nafion or Flemion, or an anion exchange membrane such as Neosepta or Selemion. As will be described later, when it is assumed that an alkaline solution is used as the anode solution and the cathode solution, and hydroxide ions ($OH^-$) move mainly, the separator 30 is preferably formed by the anion exchange membrane. However, a glass filter, a porous polymeric membrane, a porous insulating material, or the like may be applied to the separator 30, as long as they are a material capable of making ions move between the anode 11 and the cathode 22 other than the ion exchange membrane.

Each of the anode solution and the cathode solution as the electrolytic solution is preferably a solution containing at least water ($H_2O$). Because carbon dioxide ($CO_2$) is supplied from the $CO_2$ gas flow path 23, the cathode solution may or may not contain carbon dioxide ($CO_2$). The same solution or different solutions may be applied to the anode solution and the cathode solution. An example of a solution containing $H_2O$ used as the anode solution and the cathode solution includes an aqueous solution containing an arbitrary electrolyte. Examples of the aqueous solution containing the electrolyte include, for example, an aqueous solution containing at least one selected from a hydroxide ion ($OH^-$), a hydrogen ion ($H^+$), a potassium ion ($K^+$), a sodium ion ($Na^+$), a lithium ion ($Li^+$), a chloride ion ($Cl^-$), a bromide ion ($Br^-$), an iodide ion ($I^-$), a nitrate ion ($NO_3^-$), a sulfate ion ($SO_4^{2-}$), a phosphate ion ($PO_4^{2-}$), a borate ion ($BO_3^{3-}$), and a hydrogen carbonate ion ($HCO_3$). In order to reduce an electrical resistance of the electrolytic solution, it is preferable to use, as the anode solution and the cathode solution, an alkaline solution in which an electrolyte such as a potassium hydroxide or a sodium hydroxide is dissolved in high concentration.

For the cathode solution, it is also possible to use an ionic liquid which is made of salts of cations such as imidazolium ions or pyridinium ions and anions such as $BF_4^-$ or $PF_6^-$ and which is in a liquid state in a wide temperature range, or its aqueous solution. Examples of other cathode solutions include an amine solution of ethanolamine, imidazole, pyridine, or the like, or an aqueous solution thereof. Any of primary amine, secondary amine, and tertiary amine is applicable as amine.

The anode solution is supplied from the anode solution supply system 100 to the anode solution flow path 12 of the anode part 10. The anode solution supply system 100 circulates the anode solution so that the anode solution flows through inside the anode solution flow path 12. The anode solution supply system 100 has a pressure controller 101, an anode solution tank 102, a flow rate controller (pump) 103, a reference electrode 104 and a pressure gauge 105, and is configured to make the anode solution circulate in the anode solution flow path 12. The anode solution tank 102 is connected to a non-illustrated gas component collection unit which collects a gas component such as oxygen ($O_2$) contained in the circulating anode solution. The anode solution is introduced into the anode solution flow path 12 after a flow rate and a pressure thereof are controlled at the pressure controller 101 and the flow rate controller 103.

The cathode solution is supplied from the cathode solution supply system 200 to the cathode solution flow path 21 of the cathode part 20. The cathode solution supply system 200 circulates the cathode solution so that the cathode solution flows through inside the cathode solution flow path 21. The cathode solution supply system 200 has a pressure controller 201, a cathode solution tank 202, a flow rate controller (pump) 203, a reference electrode 204, and a pressure gauge 205, and is configured to make the cathode solution circulate in the cathode solution flow path 21. The cathode solution tank 202 is connected to a gas component collection unit 206 which collects a gas component such as carbon monoxide (CO) contained in the circulating cathode solution. The cathode solution is introduced into the cathode solution flow path 21 after a flow rate and a pressure thereof are controlled at the pressure controller 201 and the flow rate controller 203.

The $CO_2$ gas is supplied from the carbon dioxide source 7000 through the gas supply system 300 to the $CO_2$ gas flow path 23. The gas supply system 300 has a $CO_2$ gas cylinder 301, a flow rate controller 302, a pressure gauge 303, and a pressure controller 304. The $CO_2$ gas is introduced into the $CO_2$ gas flow path 23 after a flow rate and a pressure thereof are controlled at the flow rate controller 302 and the pressure controller 304. The gas supply system 300 is connected to the product collection system 400 which collects a product in the gas flowed through the $CO_2$ gas flow path 23. The product collection system 400 has a gas/liquid separation unit 401 and a product collection unit 402. A reduction product such as CO or $H_2$ contained in the gas flowed through the $CO_2$ gas flow path 23 is accumulated in the product collection unit 402 through the gas/liquid separation unit 401.

The anode solution and the cathode solution circulate in the anode solution flow path 12 and the cathode solution flow path 21 at a time of an electrolytic reaction operation, as described above. At a time of a later-described refresh operation of the electrolysis cell 2, the anode solution and the cathode solution are discharged to the waste solution collection system 600 so that the anode 11, the anode solution flow path 12, the cathode 22, the cathode solution flow path 21, and the like are exposed from the anode solution and the cathode solution. The waste solution collection system 600 has a waste solution collection tank 601 connected to the anode solution flow path 12 and the cathode solution flow path 21. Waste solutions of the anode solution and the cathode solution are collected into the waste solution collection tank 601 by opening and closing non-illustrated valves. The opening and closing of the valves, and the like are collectively controlled by the control system 500. The waste solution collection tank 601 also functions as a collection unit of a rinse solution supplied from the refresh material source 700. Further, a gaseous substance supplied from the refresh material source 700 and containing a part of a liquid substance, is also collected by the waste solution collection tank 601 according to need.

The refresh material source 700 includes a gaseous substance supply system 710 and a rinse solution supply system 720. Note that the rinse solution supply system 720 can be omitted according to circumstances. The gaseous substance supply system 710 has a gas tank 711 to be a supply source of a gaseous substance such as air, carbon dioxide, oxygen, nitrogen, or argon, and a pressure controller 712 which controls a supply pressure of the gaseous substance. The rinse solution supply system 720 has a rinse solution tank 721 to be a supply source of a rinse solution such as water and a flow rate controller (pump) 722 which controls a supply flow rate or the like of the rinse solution. The gaseous substance supply system 710 and the rinse solution supply system 720 are connected to the anode solution flow path 12, the cathode solution flow path 21, and the $CO_2$ gas flow path 23 through pipes. The gaseous substance and the rinse solution are supplied to each of the flow paths 12, 21, and 23 by opening and closing non-illustrated valves. The opening and closing of the valves, and the like are collectively controlled by the control system 500.

A part of the reduction product accumulated at the product collection unit 402 is transmitted to a detection unit 501 of the control system 500. The detection unit 501 acquires data defining operation states of the electrolysis cell 2. The detection unit 501 includes at least one sensor. For example, a flow rate sensor acquiring flow rate data by measuring the flow rate of the reduction product, an optical sensor acquiring spectral data by measuring spectrum of the reduction product, and so on can be used as the sensor.

Examples of the flow rate sensor include, for example, a volume flow rate sensor, a mass flow rate sensor, or the like. Examples of the volume flow rate sensor include, for example, an actual-measurement type sensor, an inferential type sensor, or the like. Examples of the actual-measurement type sensor include, for example, self type (a rotor type, a rotary piston type, a piston type, a diaphragm type, a drum type, or a rotary-vane type) sensors, a servo type sensor, and so on. Examples of the inferential type sensor include: for example, a differential-pressure type sensor such as an orifice type, a nozzle type, a venturi type; an areal sensor such as a float type or a piston type; a vortex type sensor such as a vortex-differential type, a Karman vortex type or a fluidic type; a turbine sensor; an electromagnetic sensor; an ultrasonic sensor; a laser flow speed sensor; a weir type sensor; and so on. Examples of the mass flow rate sensor include a direct sensor such as, for example, a thermal type, a coriolis type or a differential-pressure type. An example of the optical sensor includes, for example, an infrared spectral sensor, or the like.

The data defining the operation states of the electrolysis cell 2 may be formed by a plurality of types of data. The plurality of types of data may include, for example, at least one parameter selected from the group consisting of a flow rate of the reduction product discharged from the electrolysis cell 2, a spectrum of the reduction product, a voltage between the anode 11 and the cathode 22, a potential of the anode 11, a potential of the cathode 22, a pressure in the cathode solution flow path 21, a temperature of an electrolytic solution, pH of the electrolytic solution, an operating time of the electrolysis cell 2, the number of starts of the electrolysis cell 2, and the number of stops of the electrolysis cell 2.

The data defining the operation states of the electrolysis cell 2 may contain data indicating at least one parameter selected from the group consisting of an electric energy or at least a part of a power demand amount of an electrolytic system which is supplied from the power storage device 6000 to the electrolysis cell 2, an electric energy amount supplied from the renewable energy source 4000, a flow rate of carbon dioxide supplied from the carbon dioxide source 7000, and an operating state of the plant 8000. The data defining the operation states of the electrolysis cell 2 may further contain data indicating a temperature in the tank and data indicating a pressure in the tank of the compressor 2001.

At least the part of the power demand amount of the electrolytic system is, for example, the power demand amount (a current or predicted amount) of an entire or a part of systems connected to the electrolysis cell 2 or the power demand amount (a current or predicted amount) of facilities or areas whose distances are relatively near capable of electrically connected to the electrolysis cell 2. Operating the electrolysis cell 2 by using surplus power enables high-efficiency operation of a thermal power station to solve a surplus power problem inhibiting propagation of the renewable energy. Further, leveling of an electric power grid in an area becomes possible. It is preferable to regulate the electrolysis conditions of the electrolysis cell 2 in accordance with the power demand amount (the current or predicted amount) in order to take advantage of merits as stated above.

The data acquired at the detection unit 501 is transmitted to the electrolytic regulator 502 and a refresh controller 503 of the control system 500, and further transmitted to the system control device 3001. The system control device 3001 is able to store data to predict the flow rate of each product such as cell data. The system control device 3001 predicts the flow rates of the products such as a carbon compound and hydrogen discharged from the electrolysis cell 2 based on the data from the detection unit 501, and controls the regulation of the electrolysis conditions by the electrolytic regulator 502 and the regulation of the compression conditions of the reduction product by the compressor regulator 2002 in accordance with the predicted flow rates.

The electrolytic regulator 502 is electrically connected to the power controller 40, the pressure controller 101 and the flow rate controller 103 of the anode solution supply system 100, the pressure controller 201 and the flow rate controller 203 of the cathode solution supply system 200, the flow rate controller 302 and the pressure controller 304 of the gas supply system 300, and the pressure controller 712 and the flow rate controller 722 of the refresh material source 700 in addition to the detection unit 501 through partly non-illustrated bi-directional signal lines, and these are collectively controlled. Note that non-illustrated valves are provided at each pipe, and opening/closing operations of the valves are controlled by signals from the electrolytic regulator 502. The electrolytic regulator 502 may control operations of the above-stated components at, for example, an electrolysis operation time.

The refresh controller 503 is electrically connected to the power controller 40, the flow rate controller 103 of the anode solution supply system 100, the flow rate controller 203 of the cathode solution supply system 200, the flow rate controller 302 of the gas supply system 300, and the pressure controller 712 and the flow rate controller 722 of the refresh material source 700 through partly non-illustrated bi-directional signal lines, and these are collectively controlled. Note that non-illustrated valves are provided at each pipe, and opening/closing operations of the valves are controlled by signals from the refresh controller 503. The refresh controller 503 may control operations of the above-stated components at, for example, the electrolysis operation time. The refresh controller 503 may be connected to the system control device 3001. Further, the refresh controller 503 and the electrolytic regulator 502 may be formed by one controller.

The analysis unit 3002 is able to control the regulation of the electrolysis conditions of the electrolysis cell 2 by analyzing detection data transmitted to the system control device 3001, and updating request criteria of the electrolysis conditions (cell performance) of the electrolysis cell 2 and judgment criteria of necessity of the refresh operation defined by, for example, the detection data, and prediction values of the flow rate of the reduction product in accordance with the detection data. The system control device 3001 may have a learning function, and the analysis unit 3002 may collect detection data from, for example, other electrolysis cells outside the electrolytic device 1, and derive necessary parameters through big data analysis or analysis by artificial intelligence or the like to update the request criteria. Further, other data which enables optimum operation of an entire system may be similarly communicated. The electrolytic device 1 is able to be operated more efficiently if, for example, an operating time is elongated by the learning function.

Figure 12:
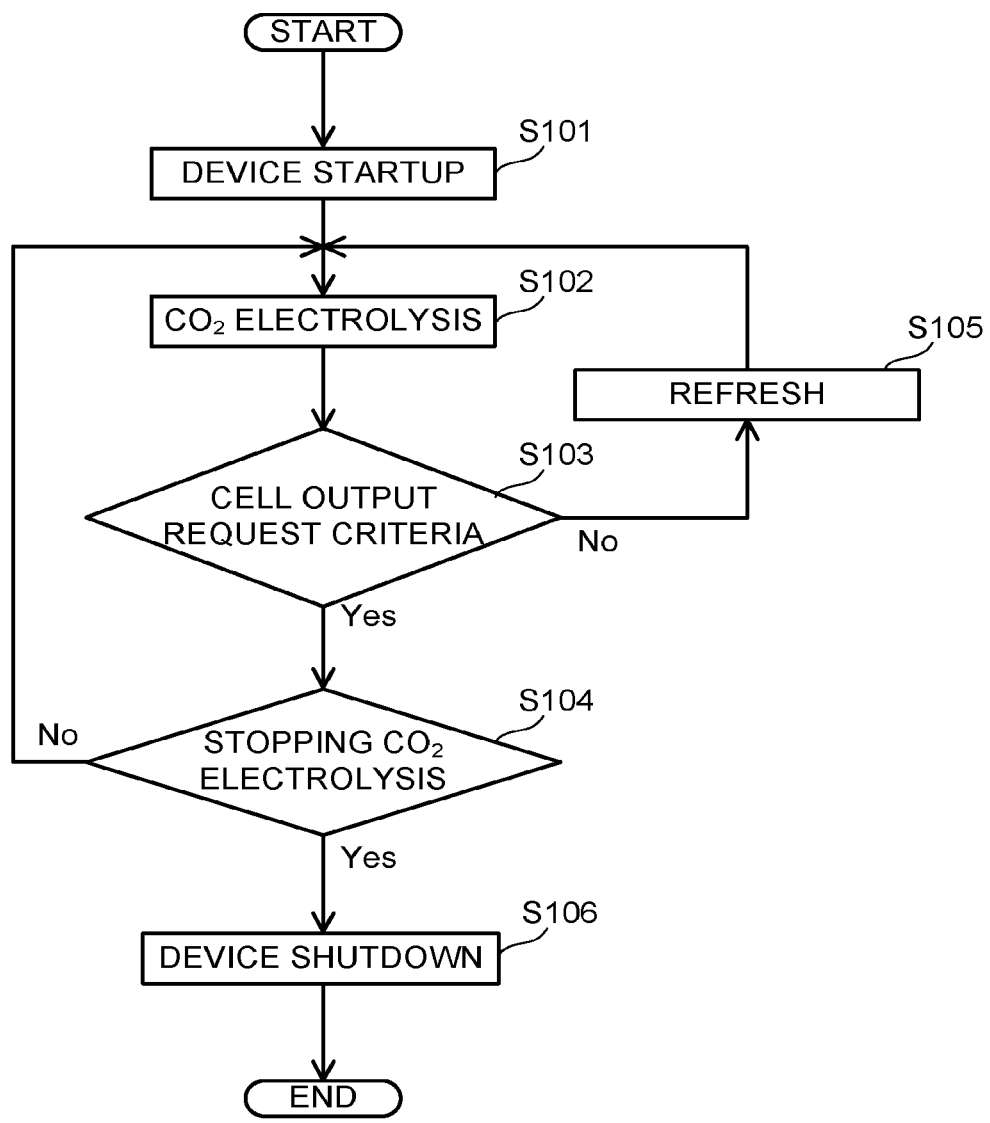
FIG. 12 is a view illustrating an operation process of the electrolytic device.

Operations of the carbon dioxide electrolytic device 1 of the embodiment will be described. First, a start-up step S101 of the electrolytic device 1 is performed as illustrated in FIG. 12. In the start-up step S101 of the electrolytic device 1, the following operations are performed. In the anode solution supply system 100, a flow rate and a pressure are controlled by the pressure controller 101 and the flow rate controller 103, and the anode solution is introduced into the anode solution flow path 12. In the cathode solution supply system 200, a flow rate and a pressure are controlled by the pressure controller 201 and the flow rate controller 203, and the cathode solution is introduced into the cathode solution flow path 21. In the gas supply system 300, a flow rate and a pressure are controlled by the flow rate controller 302 and the pressure controller 304, and $CO_2$ gas is introduced into the $CO_2$ gas flow path 23.

Next, a $CO_2$ electrolysis operation step S102 is performed. In the $CO_2$ electrolysis operation step S102, application of an electrolytic voltage is started by the power controller 40 of the electrolytic device 1 being subjected to the start-up step S101, and a current is supplied by applying the voltage between the anode 11 and the cathode 22. When the current is made to flow between the anode 11 and the cathode 22, an oxidation reaction in the vicinity of the anode 11 and a reduction reaction in the vicinity of the cathode 22 occur, which will be described below. Here, a case of generating carbon monoxide (CO) as the carbon compound is mainly described, but, the carbon compound as the reduction product of carbon dioxide is not limited to carbon monoxide, and may be other carbon compounds such as the above-described organic compounds. Further, as a reaction process caused by the electrolysis cell 2, there can be considered a case where hydrogen ions ($H^+$) are mainly produced and a case where hydroxide ions ($OH^-$) are mainly produced, but, it is not limited to either of these reaction processes.

First, the reaction process in a case of mainly oxidizing water ($H_2O$) to produce hydrogen ions ($H^+$) is described. When a current is supplied between the anode 11 and the cathode 22 from the power controller 40, an oxidation reaction of water ($H_2O$) occurs at the anode 11 which is in contact with the anode solution. Concretely, as presented in the following formula (1), $H_2O$ contained in the anode solution is oxidized, and oxygen ($O_2$) and hydrogen ions ($H^+$) are produced.

$$2H_2O \rightarrow 4H^+ + O_2 + 4e \quad (1)$$

$H^+$ produced at the anode 11 moves in the anode solution existing in the anode 11, the separator 30, and the cathode solution in the cathode solution flow path 21, and reaches the vicinity of the cathode 22. The reduction reaction of carbon dioxide ($CO_2$) occurs by electrons (e) based on the current supplied from the power controller 40 to the cathode 22 and $H^+$ moved to the vicinity of the cathode 22. Concretely, as presented in the following formula (2), $CO_2$ supplied from the $CO_2$ gas flow path 23 to the cathode 22 is reduced, and CO and $H_2O$ are produced. Further, in addition to carbon monoxide, hydrogen may be produced as presented in the following formula (3) by hydrogen ions receiving electrons. At this time, hydrogen may be produced simultaneously with carbon monoxide.

$$2CO_2 + 4H^+ + 4e^- \rightarrow 2CO + 2H_2O \quad (2)$$

$$4H^+ + 4e^- \rightarrow 2H_2 \quad (3)$$

Next, the reaction process in a case of mainly reducing carbon dioxide ($CO_2$) to produce hydroxide ions ($OH^-$) is described. When a current is supplied between the anode 11 and the cathode 22 from the power controller 40, water ($H_2O$) and carbon dioxide ($CO_2$) are reduced, and carbon monoxide (CO) and hydroxide ions ($OH^-$) are produced in the vicinity of the cathode 22, as presented in the following formula (4). The hydroxide ions ($OH^-$) diffuse to the vicinity of the anode 11, and the hydroxide ions ($OH^-$) are oxidized, and oxygen ($O_2$) is produced as presented in the following formula (5).

$$2CO_2 + 2H_2O + 4e^- \rightarrow 2CO + 4OH^- \quad (4)$$

$$4OH^- \rightarrow 2H_2O + O_2 + 4e^- \quad (5)$$

The produced gas component is compressed and accommodated by the compressor 2001. It is preferable to use a pressure tank or a liquefying tank to reduce a size of the storage tank and cost when the produced gas component is stored. For example, in a case of CO, it is practical to store in the pressure tank, and it is required to be high-pressure in consideration of subsequently making CO react with hydrogen or the like to convert into methanol or the like. In a case when ethylene or the like is produced, it is practical to store after being liquefied, and it is required to be pressurized in order to be liquefied.

When a plurality of gas components are simultaneously produced, a separation process is subsequently required, and it is necessary to separate the product in accordance with the components. In this case, it is important to predict a component ratio of produced gas. The control of the compression conditions becomes difficult when the component ratio changes. Since reactivity of the cell changes with respect to a change in the pressure to cause decrease in efficiency and the change in the component ratio to lower entire efficiency, a large change in pressure is not desirable.

When the porous membrane is used as the separator 30, liquid may flow out of the anode 11 to the cathode 22 due to a pressure difference between the anode 11 and the cathode 22, or gas moves from the cathode 22 to the anode 11. In this case, there are problems that the gas has to be separated from the anode 11, the liquid has to be separated from the cathode 22, the reduction products such as hydrogen and $CO_2$ produced in the vicinity of the cathode 22 move to the anode 11 and return to the original substances due to oxidization. The pressure difference of the cell is therefore not preferable. When the electrolyte membrane is used as the separator 30, the pressure difference is also not preferable because the membrane may be broken due to insufficient strength of the electrolyte membrane or sealant of the cell may be broken.

It can be thought to provide, for example, a gas flow rate sensor in order to make the pressure of the electrolysis cell 2 constant to control the product separation and to operate the compressor 2001, but it is difficult to measure the flow rate under a circumstance where the pressure changes and to control the separation of the products only by using the flow rate sensor. For example, when a flow rate sensor having an error in a flow rate value due to a pressure change is used, the compressor 2001 is operated in accordance with the flow rate, and it is operated so as not to generate the pressure change in the cell. Here, the pressure change in the cell occurs due to the operation of the compressor 2001 by the measurement error due to a slight amount of pressure change, further the compressor 2001 is operated by the measurement error due to the pressure change, and the error becomes large due to the repeated erroneous operations, resulting in that a stable operation becomes difficult.

It is also considered to take a method estimating a gas amount from a current value of the cell, but the current value does not necessarily correspond to the gas amount in a case of the $CO_2$ reduction because gas production amounts of CO and ethylene are different depending on the number of reacted electrons, and therefore, it is difficult to estimate the gas amount only from the current value. Further, a gas amount cannot be determined even in a reaction between hydrogen and CO where the number of electrons are the same and the current values and the gas production amounts are the same because a current flows due to a crossover phenomenon of substances between the anode 11 and the cathode 22 and the cell current value does not necessarily correspond to the gas component. Even when the current value and the gas amount match, it is not desirable in terms of use of collected gas subsequent thereto if a component ratio of produced gas is not clear. It is a very important problem to predict the component ratio (flow rate ratio) of the product in terms of the above.

It is considered to take a sample and analyze the produced gas by using a gas chromatography analyzer or the like, but it is difficult to perform constant monitoring because it is expensive and a measurement time is not short. Accordingly, it is preferable to simply predict the gas component without using an expensive device.

In the electrolytic system of the embodiment, one or more types of data defining the operation states of the electrolysis cell 2 are acquired by the detection unit 501, a flow rate of a specific reduction product is predicted based on the data by the system controller 3000, and at least one of the electrolytic regulator 502 and the compressor regulator 2002 is controlled in accordance with the predicted flow rate. Note that an entire system may be controlled in accordance with the flow rate.

When a flow rate of a carbon compound is predicted by using a plurality of types of flow rate data, a first flow rate sensor which measures a flow rate according to a first measurement method and a second flow rate sensor which measures a flow rate according to a second measurement method may be combined. The first measurement method is, for example, an actual-measurement type, and the second measurement method is, for example, an inferential type. The flow rate can be predicted from a difference between a volume flow rate sensor and a mass flow rate sensor, and the like. This is because characteristics of gas species are different between the carbon compound and hydrogen, or the like. For example, when CO and hydrogen are measured by the volume flow rate sensor (the piston type and the diaphragm type), the actual flow rates can be measured. By the float type flow rate sensor, the flow rates of CO and hydrogen can be presented by the following formulas (6) to (8). Note that viscosity of CO is set as 0.0177 mPa·s (20° C.) and viscosity of hydrogen is set as 0.088 mPa·s (20° C.).

$$Q = C_r A \sqrt{2g\Delta P/\rho} \quad (6)$$

$$\Delta P = P1 - P2 = W/a \quad (7)$$

(Q: flow rate ($m^3/h$), Cr: coefficient of discharge, g: gravitational acceleration ($m/s^2$), $\rho$: fluid density ($kg/m^3$), A: tubular area of float and taper pipe ($m^2$), a: effective area of float ($m^2$), P1: pressure just after floating (Pa), P2: pressure just before floating (Pa), W: weight subtracting buoyant force of float (kg))

$$Re = 3.54 \times 10^5 (Q/av) \quad (8)$$

(Q: flow rate ($m^3/h$), a: diameter of float, v: dynamic viscosity)

Since the coefficients of discharge are different depending on the viscosity of gas, a value of the flow rate sensor differs even at the same volume flow rate if the component ratio changes. The component ratio (flow rate ratio) between CO and hydrogen can be predicted from this difference. Note that since the differential pressure flow rate sensor using orifice can be used as a flow rate sensor by providing pressure gauges in front of and behind a flow path where a pipe diameter is changed, such a configuration is also included in the flow rate sensor.

A flow rate Q1 when the differential-pressure type flow rate sensor is used is presented by the following expression (9). Where Q1 is an actual flow rate ($m^3/h$ (ntp)), Q0 is a flow rate indicated value ($m^3/h$ (ntp)), $\mu1$ is a density of different gas ($kg/m^3$ (ntp)), $\rho0$ is a design specification density of gas ($kg/m^3$ (ntp)), P1 is a different pressure (actual operation pressure) (kPa), P0 is a design specification pressure (kPa), T1 is a different temperature (actual operation temperature) (° C.), and T0 is a design specification temperature (° C.).

[math. 1]

$$Q1 = Q0 \times \sqrt{\frac{(101.3 + P1) \times (273.2 + T0)}{(101.3 + P0) \times (273.2 + T1)}} \times \sqrt{\frac{\rho1}{\rho1}} \quad (9)$$

For example, when the density of carbon monoxide is 1.250 $kg/m^3$, the density of hydrogen is 0.0899 $kg/m^3$, the density of carbon dioxide is 1.977 $kg/m^3$ (respectively ntp), the flow rates can be predicted from these differences. For example, when the volume flow rate is 235.2 ccm and the flow rate measured by the differential-pressure flow rate sensor (for $CO_2$) indicates 212.4 ccm, it is predicted that the flow rate of carbon dioxide is 134 ccm, the flow rate of carbon monoxide is 90 ccm, and the flow rate of hydrogen is 11.2 ccm from the above calculation expression.

When Faradaic efficiency is not 100%, two gas component ratios (unknown) whose densities are different and one Faradaic efficiency F.E. (unknown) cannot be mathematically predicted accurately only by using two flow rate data. The calculation is therefore made under a condition of an impossible flow rate range, but it is also possible to estimate from data (for example, F.E.) acquired previously. It is also possible to predict by combining other measurement values (pH of the electrolytic solution or the like).

Meanwhile, when the infrared spectral sensor is used, at least one infrared light at a specific wavelength is irradiated to measure a transmission ratio, and thereby, a product amount can be measured. When an absorptance with respect to an absorption wavelength unique to the component to be measured can be measured, the component amount can be found. When there is absorption in an ultraviolet region, it is not necessary to be infrared. It is possible to predict the flow rate of a carbon compound by combining these spectroscopic methods, combining with a flow rate sensor, and combining with other data defining the operation states of the electrolysis cell 2.

When Faradaic efficiency is not 100%, two gas component ratios (unknown) whose densities are different and one Faradaic efficiency F.E. (unknown) cannot be mathematically predicted accurately only by using two flow rate data. The calculation is therefore made under a condition of an impossible flow rate range, but it is also possible to estimate from data (for example, F.E.) acquired beforehand. It is also possible to predict by combining other measurement values (pH of the electrolytic solution or the like). Further, when gas components such as CO and ethylene and liquid components such as formic acid and methanol are produced from $CO_2$, analysis becomes extremely complicated, and the flow rate of each gas component cannot be determined only by the above-stated methods. Accordingly, it is preferable to predict the flow rate of the carbon compound based on a plurality of types of data.

A gas dryer or a water remover to remove water from gas getting out of a cathode outlet of the cathode solution flow path 21 or the like may be provided at a subsequent device. For example, a water vapor amount is estimated from sensors of a temperature of the tank of the compressor 2001 and a temperature of the electrolysis cell 2, the infrared sensor, or the like, and operation conditions of the water remover and the gas dryer are set based on these values, resulting in that a thermal control of condensation and an amount of condensed water can be estimated to improve operation system efficiency. Further, troubles and efficiency lowering caused by condensation in the compressor 2001 can be prevented.

In the above-described reaction processes in the cathode 22, the reduction reaction of $CO_2$ is considered to occur in the vicinity of the boundary between the gas diffusion layer 22A and the cathode catalyst layer 22B, as described above. At this time, the cathode solution which flows through the cathode solution flow path 21 enters up to the gas diffusion layer 22A or the cathode catalyst layer 22B has excess water, which causes trouble such that the production amount of CO obtained by the reduction reaction of $CO_2$ decreases or the cell voltage increases. The lowering of the cell performance of the electrolysis cell 2 as above is also caused by not only deviation of distribution of ions and residual gas in the vicinity of the anode 11 and the cathode 22, the excess water in the cathode catalyst layer 22B, and precipitation of an electrolyte in the cathode 22 and the anode 11, but also precipitation of an electrolyte in the anode solution flow path 12 and the cathode solution flow path 21, and the like.

Further, there is a case where the electrolysis operation causes precipitation of salts in the cathode solution flow path 21 or the gas diffusion layer 22A, which blocks the flow path or decreases the gas diffusibility, resulting in that the cell performance decreases. This is because ions move between the anode 11 and the cathode 22 through the separator 30 or the ion exchange membrane, and the ions react with the gas component. For example, when a potassium hydroxide solution is used as the anode solution, and carbon dioxide gas is used as the cathode gas, potassium ions move from the anode 11 to the cathode 22, and the ions react with carbon dioxide to produce salts of potassium hydroxide, potassium carbonate, or the like. In the cathode solution flow path 21 or the gas diffusion layer 22A, the salts precipitate in the cathode solution flow path 21 or the gas diffusion layer 22A when an amount of the salts is equal to or less than solubility. When the flow path is blocked, uniform gas flow in the entire cell is prevented, and the cell performance lowers. In particular, when a plurality of cathode solution flow paths 21 are provided, the cell performance significantly lowers. Note that there is a case where the performance of the cell itself is improved by a partial increase in the gas flow rate and the like. This is because since a gas pressure is increased, the gas component or the like supplied to the catalyst increases or the gas diffusibility increases, which improves the cell performance. In order to detect the lowering of the cell performance as above, a step S103 which determines whether or not the cell performance satisfies the request criteria is performed.

The electrolytic regulator 502 collects the production amount and the proportion of each product and the cell performance such as the cell voltage, the cell current, the cathode potential, the anode potential, the pressure inside the anode solution flow path 12, the pressure inside the cathode solution flow path 21 of the electrolysis cell 2 regularly or continuously, for example, as described above. Further, in the electrolytic regulator 502, the request criteria of the cell performance are previously set, and it is determined whether or not collected data satisfy the set request criteria. When the collected data satisfy the set request criteria, the $CO_2$ electrolysis operation S102 is continued without performing a $CO_2$ electrolysis stop (S104). When the collected data do not satisfy the set request criteria, a refresh operation step S105 is performed. Note that the request criteria of the cell performance in the refresh operation may be set by using other data defining the operation states of the electrolysis cell 2.

The cell performance collected by the electrolytic regulator 502 is defined by parameters such as, for example, an upper limit value of a cell voltage when a constant current is made to flow through the electrolysis cell 2, a lower limit value of a cell current when a constant voltage is applied to the electrolysis cell 2, and Faradaic efficiency of the carbon compound produced by the reduction reaction of $CO_2$. Here, the Faradaic efficiency is defined as a proportion of a current contributing to production of an intended carbon compound with respect to an entire current flowed through the electrolysis cell 2. In order to maintain electrolysis efficiency, the refresh operation step S105 is preferably performed when the upper limit value of the cell voltage when the constant current is made to flow reaches 150% or more, preferably 120% or more of a set value. Further, the refresh operation step S105 is preferably performed when the lower limit value of the cell current at the time of applying the constant voltage reaches 50% or less, preferably 80% or less of a set value. In order to maintain a production amount of the reduction product such as the carbon compound, the refresh operation step S105 is preferably performed when the Faradaic efficiency of the carbon compound becomes 50% or less, preferably 80% or less of a set value.

Regarding the determination of the cell performance, for example, when at least one parameter from among the cell voltage, the cell current, the Faradaic efficiency of the carbon compound, the pressure inside the anode solution flow path 12, and the pressure inside the cathode solution flow path 21 does not satisfy the request criteria, it is determined that the cell performance does not satisfy the request criteria, and the refresh operation step S105 is carried out. Further, it is also possible to set the request criteria of the cell performance by combining two or more of the aforementioned parameters. For example, the refresh operation step S105 may be performed when neither the cell voltage nor the Faradaic efficiency of the carbon compound satisfies the request criteria. The refresh operation step S105 is performed when at least one of the cell performances does not satisfy the request criteria. In order to stably perform the $CO_2$ electrolysis operation step S102, the refresh operation step S105 is preferably performed at an interval of one hour or more, for example.

If the request criteria of the cell performance are judged based on only one of the cell voltage, the cell current, and the Faradaic efficiency of the carbon compound, it is sometimes judged that the refresh is necessary when salts precipitate in the flow path or the gas diffusion layer and the output is lowered, even in a case where the cell performance improves or does not change. In the electrolytic device, it is important to suspect the lowering of the cell performance beforehand and to perform the refresh operation at an optimum timing. Accordingly, in the electrolytic device of the embodiment, it is preferable that the pressure in the cell (the pressure inside the anode solution flow path 12, the pressure inside the cathode solution flow path 21, or the like) is set to one of the parameters for defining the request criteria, to thereby sense the precipitation of salts, and the refresh operation is performed.

The judgment regarding the necessity of the refresh operation is made based on not only the cell voltage, the current value, and the sensing of salts based on a pressure change in the cell, but also the performance of gas/liquid separation between the anode 11 and the cathode 22 when the anode 11 and the cathode 22 are separated by the separator 30, namely, a movement amount of the liquid or the gas between the anode 11 and the cathode 22, an amount of the product, a voltage difference relative to a reference electrode, an estimated value of the Faradaic efficiency from these parameters, and the like. The Faradaic efficiency from the respective parameter values and the necessity of the refresh operation can be comprehensively determined as judgment of the necessity of the refresh operation also from parameters to be described later, and any combination of respective values and any calculation method are applicable.

It is also possible to judge the necessity of the refresh operation based on a flooding degree estimated from respective pieces of cell data, a voltage change, and the like based on an operating method for detecting a flooding performance. Further, it is also possible to take an operating time of the electrolysis cell 2 into consideration. The operating time is not limited to an operating time after the operation is started, but may be an integrated value of the operating time so far, a duration, an operating time after the refresh operation, or further, a calculated value of multiplication between the integrated voltage value and time, or between the current value and the time, or the like, and any combination and calculation method thereof can be applied. Further, the calculated values of these combinations are preferable when compared to the judgment based on simply the duration or the like, since a difference caused by the operating method of the electrolysis cell 2 is taken into consideration. Furthermore, it is also possible to use a variation value of the current or the voltage, a pH value and a change value of the electrolytic solution, oxygen generation amount and variation amount.

It is preferable that the operation of judging the necessity of the refresh operation is performed, and the judgment is made based on the parameter such as a cell voltage at a time of the operation, since it is possible to accurately judge the necessity of the refresh operation, although the working operation time decreases. Note that a judgment time of the necessity of the refresh operation in this case is preferably at least a half or less, more preferably ¼ or less, and ideally ⅒ or less of a refresh operation time. Further, regarding the respective parameters for judging the necessity of the refresh operation, respective pieces of data of the electrolysis cell 2 are collected through an electronic network, required parameters are derived by the electrolytic regulator 502 and the analysis part 3002 of a plurality of cells, through big data analysis, and analysis of machine learning or the like, the refresh controller 503 is made to update the request criteria of the cell performance defined by the respective parameters for judging the necessity of refresh, and it is possible to constantly perform the best refresh operation.

Figure 13:
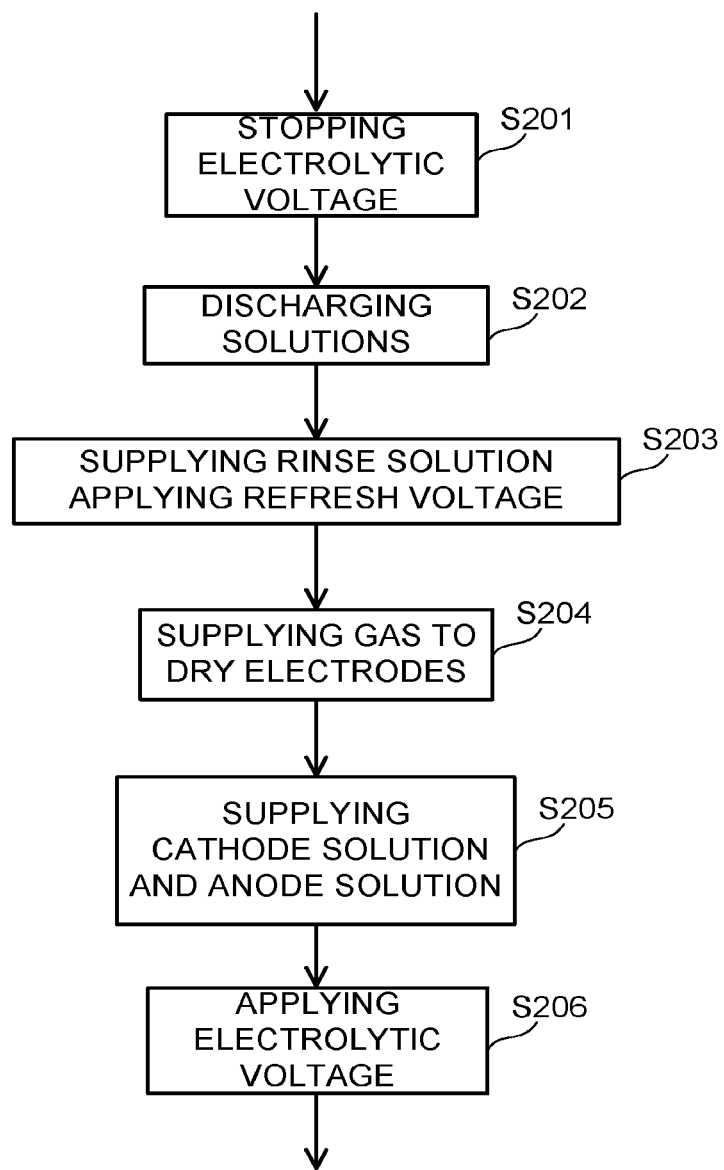
FIG. 13 is a view illustrating a refresh process of the electrolytic device.

The refresh operation step S105 is performed according to a flow chart illustrated in FIG. 13, for example. First, the application of the electrolytic voltage performed by the power controller 40 is stopped, to thereby stop the reduction reaction of $CO_2$ (S201). At this time, the application of the electrolytic voltage does not necessarily have to be stopped. Next, the cathode solution and the anode solution are discharged from the cathode solution flow path 21 and the anode solution flow path 12 (S202). Next, the rinse solution is supplied to the cathode solution flow path 21 and the anode solution flow path 12 (S203), to thereby perform washing. While the rinse solution is supplied, a refresh voltage may be applied between the anode 11 and the cathode 22. This makes it possible to remove ions and impurities adhered to the cathode catalyst layer 22B. When the refresh voltage is applied so as to perform mainly oxidation treatment, ions and impurities such as organic matters adhered to the surface of the catalyst are oxidized to be removed. Further, by performing this treatment in the rinse solution, it is possible to perform not only the refresh of the catalyst but also removal of ions substituted in an ion-exchange resin in a case of using the ion exchange membrane as the separator 30.

The refresh voltage is preferably −2.5 V or more and 2.5 V or less, for example. Since energy is used for the refresh operation, the range of the refresh voltage is preferably as narrow as possible, and the range is more preferably −1.5 V or more and 1.5 V or less, for example. The refresh voltage may be cyclically applied so that the oxidation treatment and the reduction treatment of the ions and the impurities are alternately performed. This makes it possible to accelerate regeneration of the ion-exchange resin and regeneration of the catalyst. Further, it is also possible to perform the refresh operation by applying, as the refresh voltage, a voltage whose value is equal to that of the electrolytic voltage at a time of the electrolysis operation. In this case, it is possible to simplify the configuration of the power controller 40.

Next, gas is supplied to the cathode solution flow path 21 and the anode solution flow path 12 (S204), to thereby dry the cathode 22 and the anode 11. When the rinse solution is supplied to the cathode solution flow path 21 and the anode solution flow path 12, a saturation degree of water in the gas diffusion layer 22A increases and output lowering occurs due to the diffusibility of gas. By supplying the gas, the saturation degree of water lowers, so that the cell performance is recovered, and a refresh effect is increased. The gas is preferably supplied right after the rinse solution is made to flow, and is preferably supplied at least within five minutes after the finish of supply of the rinse solution. This is because the output lowering is large due to the increase in the saturation degree of water, and if it is assumed that the refresh operation is performed at intervals of an hour, for example, an output during the refresh operation in five minutes is 0 V or significantly small, so that 5/60 of the output is sometimes lost.

When the above refresh operation finishes, the cathode solution is introduced into the cathode solution flow path 21, the anode solution is introduced into the anode solution flow path 12, and $CO_2$ gas is introduced into the $CO_2$ gas flow path 23 (S205). Subsequently, the application of the electrolytic voltage between the anode 11 and the cathode 22 performed by the power controller 40 is resumed, to thereby resume the $CO_2$ electrolysis operation (S206). Note that when the application of the electrolytic voltage is not stopped in S201, the aforementioned resume operation is not performed. For the discharge of the cathode solution and the anode solution from each of the flow paths 12 and 21, gas may be used or the rinse solution may be used.

The supply and flow of the rinse solution (S203) are performed for the purpose of preventing precipitation of an electrolyte contained in the cathode solution and the anode solution, and washing the cathode 22, the anode 11, and each of the flow paths 12 and 21. For this reason, water is preferable as the rinse solution, water having an electric conductivity of 1 mS/m or less is more preferable, and water having the electric conductivity of 0.1 mS/m or less is still more preferable. In order to remove a precipitate such as the electrolyte in the cathode 22, the anode 11, and the like, an acid rinse solution having a low concentration, of sulfuric acid, nitric acid, hydrochloric acid, or the like may be supplied, and the electrolyte may be dissolved by using the acid rinse solution. When the acid rinse solution having a low concentration is used, a step in which the rinse solution of water is supplied is performed in a subsequent step. It is preferable to perform the supply step of the rinse solution of water in order to prevent an additive contained in the rinse solution from remaining right before the gas supply step. FIG. 2 illustrates the rinse solution supply system 720 having one rinse solution tank 721, but when a plurality of rinse solutions such as water and the acid rinse solution are used, a plurality of rinse solution tanks 721 corresponding thereto are used.

In particular, for the refresh of the ion-exchange resin, acid or alkaline rinse solution is preferable. This provides an effect of discharging cations or anions substituted in place of protons or OH⁻ in the ion-exchange resin. For this reason, it is preferable that the acid rinse solution and the alkaline rinse solution are made to flow alternately, the rinse solution is combined with water having the electric conductivity of 1 mS/m or less, and gas is supplied between supplies of a plurality of rinse solutions so that the rinse solutions are not mixed.

Water produced through a reaction may also be used as the rinse solution. For example, when CO is produced from $CO_2$ and protons through reduction, water is generated. It is possible that the water discharged from the cathode 22 at this time is separated through gas/liquid separation, and stored to be used. If it is designed as above, there is no need to newly supply the rinse solution from the outside, which is advantageous in terms of a system. Further, by changing a potential to increase a reaction current, and increasing an amount of water to be produced, the water may also be supplied to the cathode solution flow path 21. Accordingly, the tank for the generated water, and the pipe, the pump, and the like used for the rinse solution become unnecessary, which provides a configuration that is effective in terms of the system. Further, it is also possible that gas containing oxygen is supplied to the cathode solution flow path 21 and a voltage is applied, to thereby perform water decomposition on the electrolytic solution or the rinse solution of the anode 11, and the refresh operation is performed by using water produced by the catalyst from protons or OH ions moved to a counter electrode. For example, in a case where Nafion is used as an ion-exchange membrane in an electrolysis cell in which $CO_2$ is reduced to CO by using a gold catalyst, when air flows through the cathode 22 and a potential is applied to the cell to perform water decomposition, protons moved to the cathode 22 are reacted with oxygen by the catalyst, and water is generated. The refresh operation can be performed by using the generated water. Further, it is also possible that hydrogen gas is generated by supplying gas containing no oxygen to the cathode 22 or stopping the supply of gas thereafter, and the generated hydrogen is used to perform the refresh operation to dry the cathode 22. It is also possible to perform the refresh operation of the catalyst by using reducing power of protons and hydrogen.

The gas used for the gas supply and the flow step S204 preferably contains at least one of air, carbon dioxide, oxygen, nitrogen, and argon. Moreover, gas having low chemical reactivity is preferably used. From such a point, air, nitrogen, and argon are preferably used, and nitrogen and argon are more preferable. The supply of the rinse solution and gas for refresh is not limited only to the cathode solution flow path 21 and the anode solution flow path 12, and the rinse solution and the gas may be supplied to the $CO_2$ gas flow path 23 in order to wash a surface of the cathode 22 which is in contact with the $CO_2$ gas flow path 23. It is effective to supply the gas to the $CO_2$ gas flow path 23 in order to dry the cathode 22 also from the side of the surface which is in contact with the $CO_2$ gas flow path 23.

The above is the description regarding the case where the rinse solution and gas for refresh are supplied to both the anode part 10 and the cathode part 20, but, the rinse solution and gas for refresh may be supplied to only one of the anode part 10 and the cathode part 20. For example, the Faradaic efficiency of the carbon compound varies depending on a contact region between the cathode solution and $CO_2$ at the gas diffusion layer 22A and the cathode catalyst layer 22B of the cathode 22. In such a case, only by supplying the rinse solution and gas for refresh to only the cathode part 20, the Faradaic efficiency of the carbon compound is sometimes recovered. Depending on a type of the electrolytic solutions (anode solution and cathode solution) to be used, there is sometimes a tendency that precipitation easily occurs in one of the anode part 10 and the cathode part 20. Based on such a tendency of the electrolytic device 1, the rinse solution and gas for refresh may be supplied to only one of the anode part 10 and the cathode part 20. Moreover, depending on operating time or the like of the electrolytic device 1, the cell performance is sometimes recovered only by drying the anode 11 and the cathode 22. In such a case, it is also possible to supply only the gas for refresh to at least one of the anode part 10 and the cathode part 20. The refresh operation step S105 can be changed in various ways according to an operation condition, a tendency, and the like of the electrolytic device 1.

As described above, in the electrolytic device 1 of the embodiment, based on whether or not the cell performance of the electrolysis cell 2 satisfies the request criteria, it is determined whether the $CO_2$ electrolysis operation step S102 is continued or the refresh operation step S105 is performed. By supplying the rinse solution and gas for refresh in the refresh operation step S105, the entry of the cathode solution into the gas diffusion layer 22A, the excess water of the cathode catalyst layer 22B, the deviation of the distribution of the ions and the residual gas in the vicinity of the anode 11 and the cathode 22, the precipitation of the electrolyte at the cathode 22, the anode 11, the anode solution flow path 12, and the cathode solution flow path 21, and the like, which become causes of lowering the cell performance, are removed. Therefore, by resuming the $CO_2$ electrolysis operation step S102 after the refresh operation step S105, the cell performance of the electrolysis cell 2 can be recovered. By repeating the $CO_2$ electrolysis operation step S102 and the refresh operation step S105 as above based on the request criteria of the cell performance, it becomes possible to maintain the $CO_2$ electrolysis performance obtained by the electrolytic device 1 for a long period of time.

Figure 14:
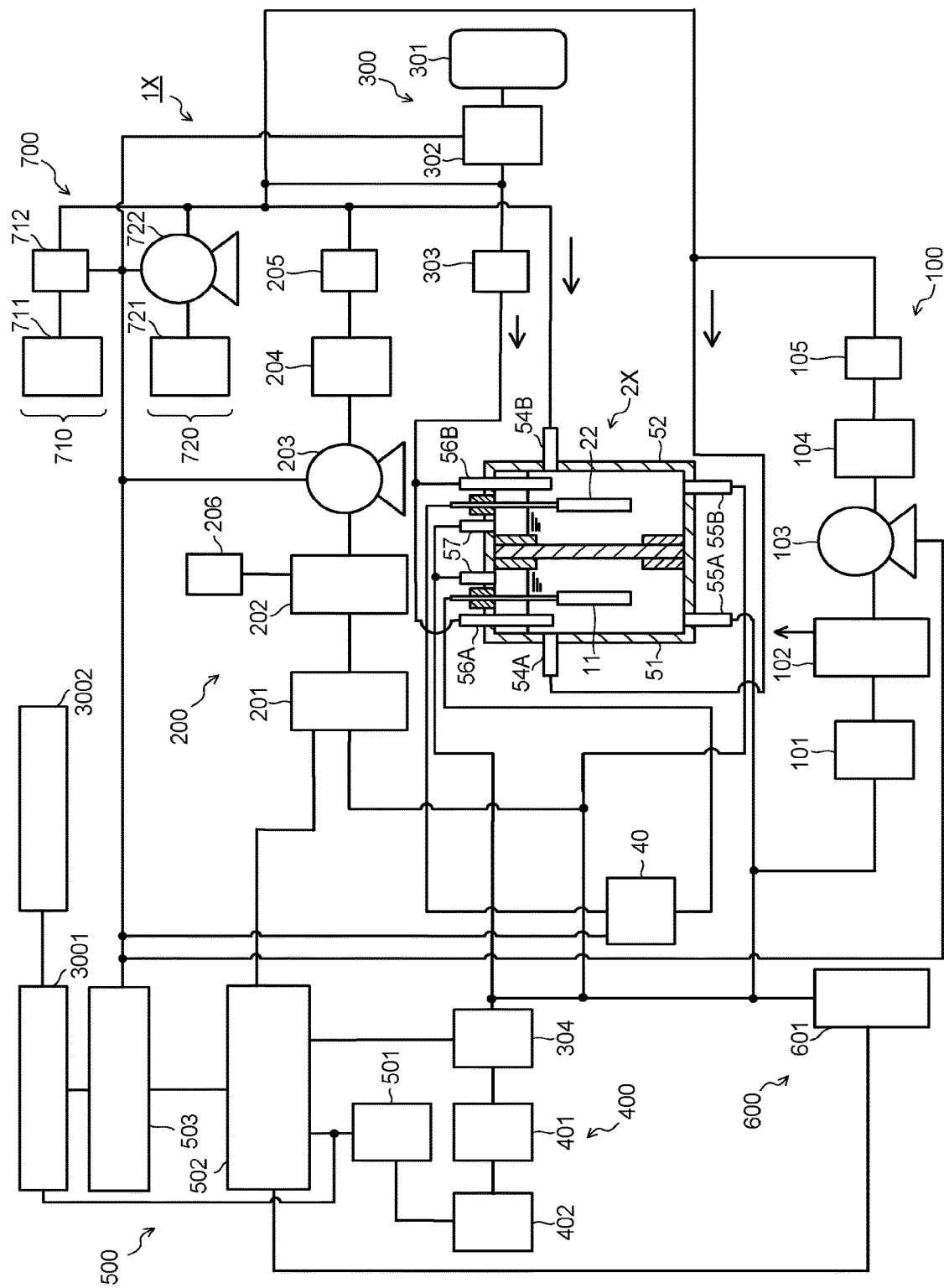
FIG. 14 is a view illustrating a configuration example of the electrolytic device.
Figure 15:
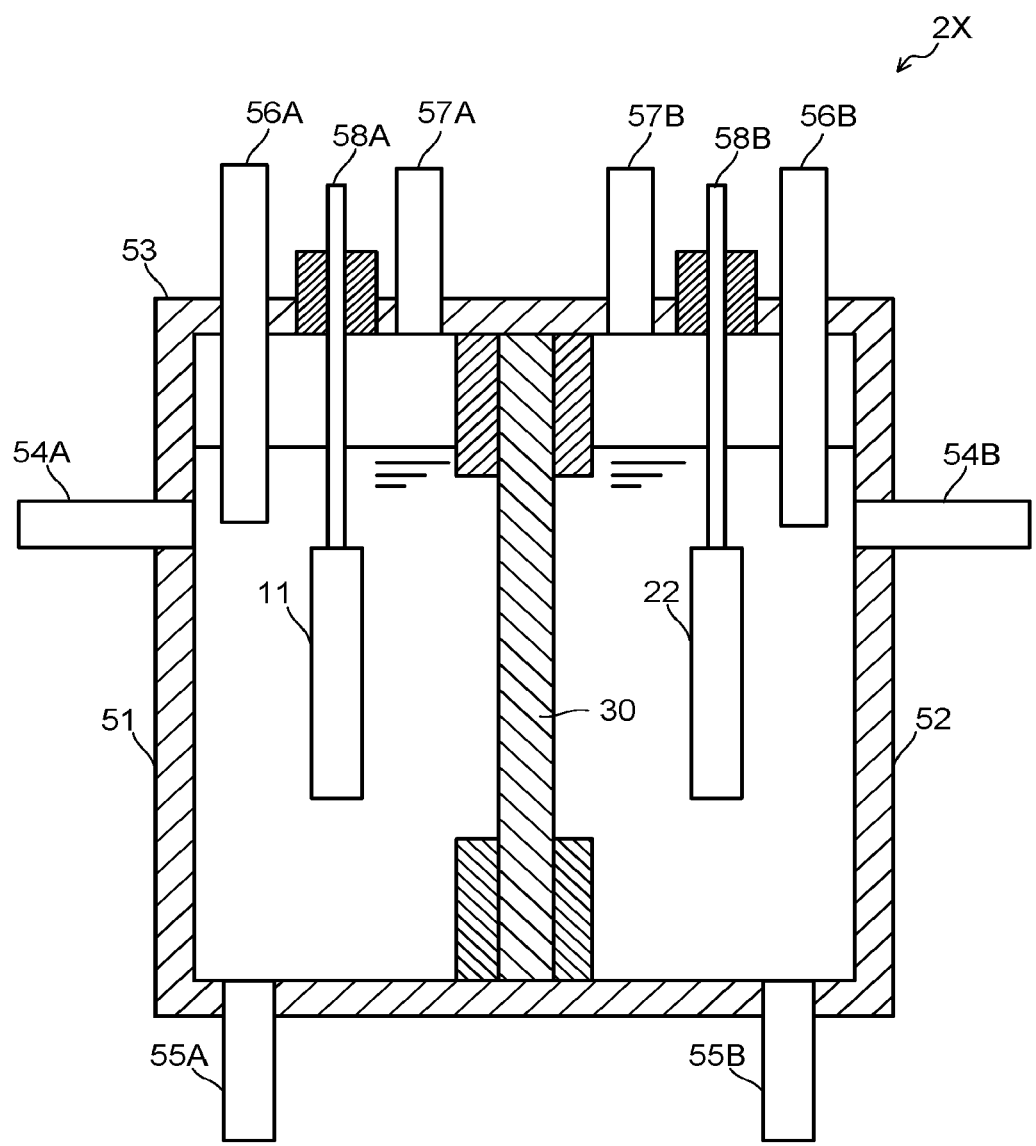
FIG. 15 is a sectional view illustrating a configuration example of the electrolysis cell.

FIG. 14 is a view illustrating a configuration of a carbon dioxide electrolytic device according to an embodiment, and FIG. 15 is a sectional view illustrating a configuration of an electrolysis cell in the electrolytic device illustrated in FIG. 14. A carbon dioxide electrolytic device 1X illustrated in FIG. 14 includes an electrolysis cell 2X, an anode solution supply system 100 which supplies an anode solution to the electrolysis cell 2X, a cathode solution supply system 200 which supplies a cathode solution to the electrolysis cell 2X, a gas supply system 300 which supplies carbon dioxide ($CO_2$) gas to the electrolysis cell 2X, a product collection system 400 which collects a product produced by a reduction reaction at the electrolysis cell 2X, a control system 500 which detects a type and a production amount of the collected product, and performs control of the product and control of a refresh operation, a waste solution collection system 600 which collects a waste solution of the cathode solution and the anode solution, and a refresh material source 700 which recovers an anode, a cathode, or the like of the electrolysis cell 2X, similarly to the carbon dioxide electrolytic device 1.

The carbon dioxide electrolytic device 1X illustrated in FIG. 14 basically includes a configuration similar to that of the electrolytic device 1 illustrated in FIG. 1, except that a configuration of the electrolysis cell 2X is different. As illustrated in FIG. 15, the electrolysis cell 2X includes a reaction tank 53 having an anode solution tank 51, a cathode solution tank 52, and a separator 30 separating the anode solution tank 51 and the cathode solution tank 52. The anode solution tank 51 has a solution inlet port 54A and a solution discharge port 55A connected to the anode solution supply system 100, and a gas inlet port 56A and a gas discharge port 57A. The anode solution is introduced and discharged from the anode solution supply system 100 to the anode solution tank 51. The anode 11 is disposed in the anode solution tank 51 so as to be immersed in the anode solution. The anode 11 is connected to a power controller 40 through a current introduction part 58A. Regulations of electrolysis conditions of the electrolysis cell 2X and compression conditions of a reduction product may be controlled as same as the electrolytic device 1.

The cathode solution tank 52 has a solution inlet port 54B and a solution discharge port 55B connected to the cathode solution supply system 200, and a gas inlet port 56B and a gas discharge port 57B connected to the gas supply system 300. The cathode solution is introduced and discharged from the cathode solution supply system 200 to the cathode solution tank 52. Further, the $CO_2$ gas is introduced from the gas supply system 300 to the cathode solution tank 52 and the gas containing a gaseous product is transmitted to the product collection system 400. The $CO_2$ gas is preferably discharged from the gas inlet port 56B into the cathode solution in order to increase solubility of the $CO_2$ gas in the cathode solution. The cathode 22 is disposed in the cathode solution tank 52 so as to be immersed in the cathode solution. The cathode 22 is connected to the power controller 40 through a current introduction part 58B.

A gaseous substance supply system 710 of the refresh material source 700 is connected to the gas inlet port 56A of the anode solution tank 51 and the gas inlet port 56B of the cathode solution tank 52 through pipes. A rinse solution supply system 720 of the refresh material source 700 is connected to the solution inlet port MA of the anode solution tank 51 and the solution inlet port 54B of the cathode solution tank 52 through pipes. The solution discharge port 55A of the anode solution tank 51 and the solution discharge port 55B of the cathode solution tank 52 are connected to the waste solution collection system 600 through pipes. The gas discharge port 57A of the anode solution tank 51 and the gas discharge port 57B of the cathode solution tank 52 are connected to the waste solution collection system 600 through pipes, to be collected in a non-illustrated waste gas collection tank through the waste solution collection system 600, or discharged into the atmosphere. Composing materials of the respective parts or the like are similar to those of the electrolytic device 1, and details thereof are as described above.

In the electrolytic device 1X, a start-up step S101 of the electrolytic device 1X and a $CO_2$ electrolysis operation step S102 are performed in a similar manner to the electrolytic device 1, except that supply modes of an anode solution, a cathode solution, and $CO_2$ gas are different. A determination step S103 regarding whether or not request criteria of cell performance are satisfied, and a flow rate prediction of a reduction product are also performed in a similar manner to the electrolytic device 1. When it is determined that the cell performance does not satisfy the request criteria, a refresh operation step S105 is performed. In the electrolytic device 1X, the refresh operation step S105 is performed as follows.

First, a $CO_2$ reduction reaction is stopped. Next, the anode solution and the cathode solution are discharged from the anode solution tank 51 and the cathode solution tank 52. At this time, application of an electrolytic voltage performed by the power controller 40 may be maintained or stopped. Next, a rinse solution is supplied from the rinse solution supply system 720 to the anode solution tank 51 and the cathode solution tank 52, to thereby wash the anode 11 and the cathode 22. While the rinse solution is supplied, a refresh voltage may be applied between the anode 11 and the cathode 22. Next, gas is supplied from the gaseous substance supply system 710 to the anode solution tank 51 and the cathode solution tank 52, to thereby dry the anode 11 and the cathode 22. The gas and the rinse solution used for the refresh operation step S105 are similar to those in the aforementioned embodiment. When the above refresh operation finishes, the anode solution is introduced into the anode solution tank 51, the cathode solution is introduced into the cathode solution tank 52, and further $CO_2$ gas is supplied into the cathode solution. Subsequently, the $CO_2$ electrolysis operation is resumed. When the application of the electrolytic voltage performed by the power controller 40 is stopped, the application is resumed. Gas may be used or the rinse solution may be used to discharge the cathode solution and the anode solution from each of the solution tanks 51, 52. Note that amounts of the cathode solution and the anode solution are larger compared to the aforementioned embodiment. It is preferable to supply the rinse solution after the solutions are discharged by using the gas in order to reduce the time for the refresh operation.

In the electrolytic device 1X, the refresh operation may also be performed as follows. The current introduction parts 58 (58A, 58B) provided at an upper part of the electrolysis cell 2X are detached, the anode 11 and the cathode 22 are taken to the outside to be exposed from the anode solution and the cathode solution. Next, the anode 11 and the cathode 22 are immersed in the rinse solution to be washed. While they are immersed in the rinse solution, the refresh voltage is applied between the anode 11 and the cathode 22 similarly to the aforementioned embodiment. Next, the anode 11 and the cathode 22 are taken out of the rinse solution and dried by spraying gas. Next, the current introduction parts 58 (58A, 58B) are attached and the anode 11 and the cathode 22 are immersed in the anode solution and the cathode solution. The $CO_2$ electrolysis operation is resumed. It is thereby possible to shorten the time for the refresh operation because the discharge and the introduction of the anode solution and the cathode solution from/to the anode solution tank 51 and the cathode solution tank 52 are omitted.

Also in the electrolytic device 1X, it is determined whether the $CO_2$ electrolysis operation is continued or the refresh operation is performed based on whether or not the cell performance of the electrolysis cell 2X satisfies the request criteria. By supplying the rinse solution and the gas in the refresh operation step, the deviation of the distribution of the ions and the residual gas in the vicinity of the anode 11 and the cathode 22, which becomes causes of lowering the cell performance, is solved, and the precipitation of the electrolyte at the anode 11 and the cathode 22, and the like are removed. Therefore, the cell performance of the electrolysis cell 2X can be recovered by resuming the $CO_2$ electrolysis operation after the refresh operation step. It becomes possible to maintain the $CO_2$ electrolysis performance obtained by the electrolytic device 1X for a long period of time by repeating the $CO_2$ electrolysis operation and the refresh operation as above based on the request criteria of the cell performance.

Figure 16:
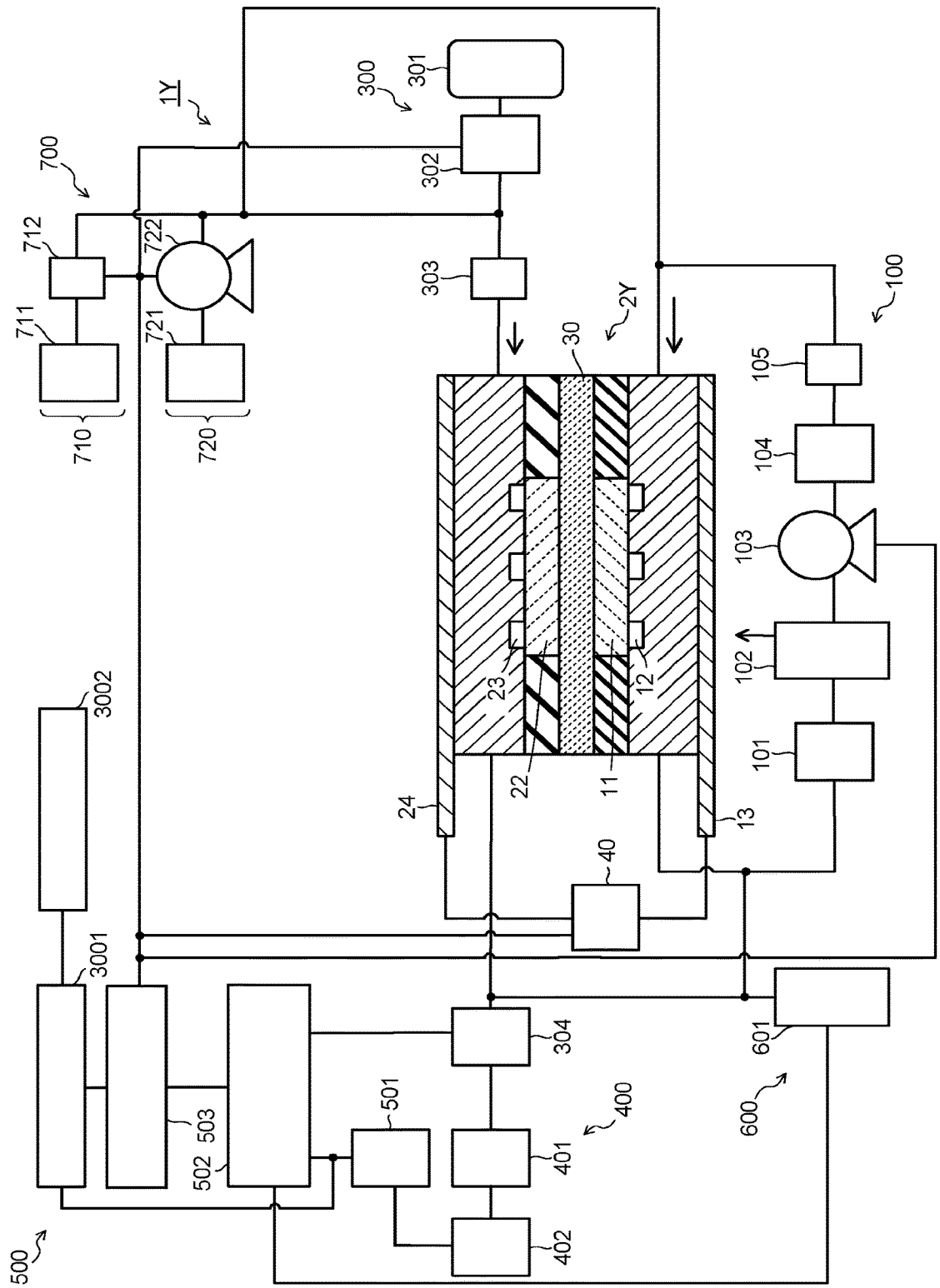
FIG. 16 is a view illustrating a configuration example of the electrolytic device.
Figure 17:
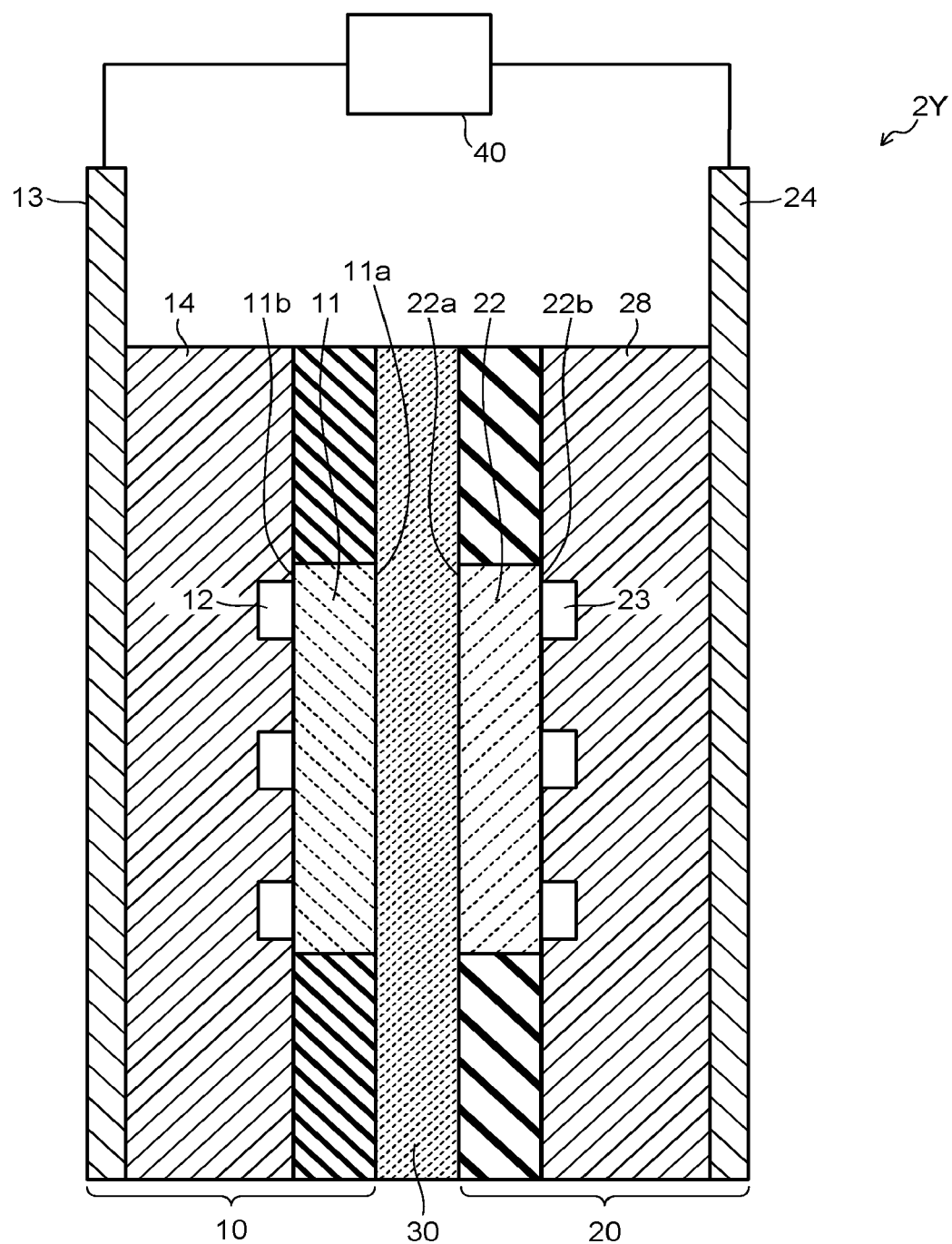
FIG. 17 is a sectional view illustrating a configuration example of the electrolysis cell.

FIG. 16 is a view illustrating another configuration example of a carbon dioxide electrolytic device according to an embodiment, and FIG. 17 is a sectional view illustrating another configuration example of an electrolysis cell in the electrolytic device illustrated in FIG. 16. A carbon dioxide electrolytic device 1Y illustrated in FIG. 16 includes an electrolysis cell 2Y, an anode solution supply system 100 which supplies an anode solution to the electrolysis cell 2Y, a gas supply system 300 which supplies carbon dioxide ($CO_2$) gas to the electrolysis cell 2Y, a product collection system 400 which collects a product produced by a reduction reaction at the electrolysis cell 2Y, a control system 500 which detects a type and a production amount of the collected product, and performs control of the product and control of a refresh operation, a waste solution collection system 600 which collects a waste solution of the anode solution, and a refresh material source 700 which recovers an anode, a cathode, or the like of the electrolysis cell 2Y, similarly to the carbon dioxide electrolytic device 1.

Besides, regulations of electrolysis conditions of the electrolysis cell 2Y and compression conditions of the reduction product may be controlled similarly to the electrolytic device 1.

The carbon dioxide electrolytic device 1Y illustrated in FIG. 16 basically includes a configuration similar to the electrolytic device 1 illustrated in FIG. 1 except that a configuration of the electrolysis cell 2Y is different and a cathode solution supply system 200 is not included. The electrolysis cell 2Y includes an anode part 10, a cathode part 20, and a separator 30 as illustrated in FIG. 17. The anode part 10 includes an anode 11, an anode solution flow path 12, and an anode current collector 13. The cathode part 20 includes a cathode 22, a $CO_2$ gas flow path 23, and a cathode current collector 24. A power controller 40 is connected to the anode 11 and the cathode 22 through a current introduction member.

The anode 11 preferably has a first surface 11a which is in contact with the separator 30, and a second surface 11b which faces the anode solution flow path 12. The first surface 11a of the anode 11 is in close contact with the separator 30. The anode solution flow path 12 is formed by a pit (groove part/recessed part) provided at a flow path plate 14. The anode solution flows through inside the anode solution flow path 12 so as to be in contact with the anode 11. The anode current collector 13 is electrically in contact with a surface on a side opposite to the anode 11 of the flow path plate 14 which forms the anode solution flow path 12. The cathode 22 has a first surface 22a which is in contact with the separator 30 and a second surface 22b which faces the $CO_2$ gas flow path 23. The $CO_2$ gas flow path 23 is formed by a pit (groove part/recessed part) provided in a flow path plate 28. The cathode current collector 24 is electrically in contact with a surface on a side opposite to the cathode 22 of the flow path plate 28 which forms the $CO_2$ gas flow path 23.

A gaseous substance supply system 710 and a rinse solution supply system 720 of the refresh material source 700 are connected to the anode solution flow path 12 and the $CO_2$ gas flow path 23 through pipes. The anode solution flow path 12 and the $CO_2$ gas flow path 23 are connected to the waste solution collection system 600 through pipes. Rinse solutions discharged from the anode solution flow path 12 and the $CO_2$ gas flow path 23 are collected by a waste solution collection tank 601 of the waste solution collection system 600. Gas for refresh discharged from the anode solution flow path 12 and the $CO_2$ gas flow path 23 is collected in a non-illustrated waste gas collection tank through the waste solution collection system 600, or discharged into the atmosphere. Composing materials of the respective parts or the like are similar to those of the electrolytic device 1, and details thereof are as described above.

In the electrolytic device 1Y, a start-up step S101 of the electrolytic device 1Y and a $CO_2$ electrolysis operation step S102 are performed in a similar manner to the electrolytic device 1, except that supply of a cathode solution is not performed. Note that a reduction reaction of $CO_2$ at the cathode 22 is performed between $CO_2$ supplied from the $CO_2$ gas flow path 23 and the anode solution permeated the cathode 22 through the separator 30. A determination step S103 regarding whether or not the request criteria of the cell performance are satisfied, and a flow rate prediction of a reduction product are also performed in a similar manner to the electrolytic device 1 of the embodiment. When it is determined that the cell performance does not satisfy the request criteria, a refresh operation step S105 is performed. In the electrolytic device 1Y, the refresh operation step S105 is performed as follows.

First, a $CO_2$ reduction reaction is stopped. At this time, application of an electrolytic voltage performed by the power controller 40 may be maintained or stopped. Next, the anode solution is discharged from the anode solution flow path 12. Next, a rinse solution is supplied from the rinse solution supply system 720 to the anode solution flow path 12 and the $CO_2$ gas flow path 23, to thereby wash the anode 11 and the cathode 22. While the rinse solution is supplied, a refresh voltage may be applied between the anode 11 and the cathode 22 as same as the aforementioned embodiment. Next, gas is supplied from the gaseous substance supply system 710 to the anode solution flow path 12 and the $CO_2$ gas flow path 23, to thereby dry the anode 11 and the cathode 22. The gas and the rinse solution used for the refresh operation step are similar to those in the aforementioned embodiment. When the above refresh operation finishes, the anode solution is introduced into the anode solution flow path 12, and $CO_2$ gas is supplied to the $CO_2$ gas flow path 23. Subsequently, the $CO_2$ electrolysis operation is resumed. When the application of the electrolytic voltage performed by the power controller 40 is stopped, the application is resumed.

Also in the electrolytic device 1Y, it is determined whether the $CO_2$ electrolysis operation is continued or the refresh operation is performed based on whether or not the cell performance of the electrolysis cell 2Y satisfies the request criteria. By supplying the rinse solution and the gas in the refresh operation step, the deviation of the distribution of the ions in the vicinity of the anode 11 and the cathode 22, which becomes causes of lowering the cell performance, is solved, and the excess water in the cathode 22, the precipitation of the electrolyte in the anode 11 and the cathode 22, the flow path block thereby, and the like are removed. Therefore, by resuming the $CO_2$ electrolysis operation after the refresh operation step, the cell performance of the electrolysis cell 2Y can be recovered. By repeating the $CO_2$ electrolysis operation and the refresh operation as above based on the request criteria of the cell performance, it becomes possible to maintain the $CO_2$ electrolysis performance obtained by the electrolytic device 1Y for a long period of time.

When liquid passes through the separator 30 at a relatively low pressure, for example, a hydrophilic polytetrafluoroethylene (PTFE) porous body or the like is used, the rinse solution is supplied to only the anode solution flow path 12, and a pressure is applied to the liquid at an anode outlet by using a non-illustrated valve or the like or the anode outlet is blocked. Accordingly, the rinse solution passes through the separator 30, flows into the cathode 22, and the rinse solution flows out from a discharge port of the cathode 22. This makes it possible to perform the refresh of the cathode 22 and the refresh of the anode 11 at the same time. This configuration eliminates the necessity of the device which makes the rinse solution flow through the cathode 22 so that the device becomes compact in size, and further, the system is simplified, which is preferable.

Note that a pipe through which air gas is introduced into the cathode 22 may be connected to the cathode 22. At a time of the refresh, it is possible that gas containing air is supplied to the cathode 22, and a refresh voltage is applied between the anode 11 and the cathode 22, to thereby cause a water electrolytic reaction. On the anode 11 side, oxygen is generated by an oxidation catalyst, and generated protons move to the cathode 22 through the separator 30 or an electrolyte membrane. At the cathode 22, the protons and oxygen in the air are reacted by a cathode catalyst, resulting in that water is generated. By using the generated water, salts in the cathode can be dissolved to be discharged. Further, the generated water is pure water, so that it can be used to wash the cathode 22. At this time, impurities in the cathode 22 can be subjected to reduction treatment by using the protons moved to the cathode 22, and it is possible to regenerate the catalyst and the members. This configuration eliminates the necessity of the device which supplies the rinse solution to the cathode 22 so that the device becomes compact in size, and further, the system is simplified, which is preferable. Further, when, before the flow of the $CO_2$ gas to be performed thereafter, the air flowed through the cathode is stopped, the generated protons react with each other to generate hydrogen, which also enables to push out generated water. When the oxygen-containing gas is stopped before performing push with $CO_2$, a regeneration function of the catalyst and the members provided by the protons can become more effective. This is because other catalysts which are difficult to be reduced and the respective members of the cathode 22 are reduced, due to the absence of oxygen. Concretely, examples of organic matters of impurities include metal oxides and the like. When $CO_2$ is supplied thereafter to cause a reaction, it is possible to further expect the refresh effect.

EXAMPLE

Example 1

An electrolytic device illustrated in FIG. 16 was fabricated, and an electrolysis performance of carbon dioxide was examined. First, on a carbon paper provided with a porous layer, a cathode to which carbon particles on which gold nanoparticles were supported were applied, was produced by the following procedure. A coating solution in which the carbon particles on which the gold nanoparticles were supported, pure water, a Nafion solution, and ethylene glycol were mixed was produced. An average particle diameter of the gold nanoparticles was 8.7 nm, and a supported amount thereof was 18.9 mass %. The coating solution was filled in an airbrush and spray-coated on the carbon paper provided with the porous layer, by using Ar gas. After the coating, washing was performed by flowing pure water for 30 minutes, and thereafter, organic matters such as ethylene glycol were oxidized to be removed through immersion in a hydrogen peroxide solution. This was cut into a size of 2×2 cm to be set as the cathode. Note that a coating amount of Au was estimated as about 0.2 mg/cm$^2$ from a mixing amount of the gold nanoparticles and the carbon particles in the coating solution. For an anode, an electrode in which $IrO_2$ nanoparticles to be a catalyst were applied to Ti mesh was used. As the anode, one in which $IrO_2$/Ti mesh was cut into 2×2 cm was used.

As illustrated in FIG. 17, the electrolysis cell 2 was produced in a manner that the cathode current collector 24, the $CO_2$ gas flow path 23 (the third flow path plate 28), the cathode 22, the separator 30, the anode 11, and the anode solution flow path 12 (the anode current collector 13) were stacked in this order from the top, the stack was sandwiched by non-illustrated support plates, and tightened with bolts. For the separator 30, an anion exchange membrane (product name: Selemion, manufactured by ASAHI GLASS CO., LTD.) was used. The $IrO_2$/Ti mesh of the anode 11 was brought into close contact with the anion exchange membrane. Note that an evaluation temperature was set to room temperature.

The electrolytic device was operated under the following conditions. $CO_2$ gas was supplied to the $CO_2$ gas flow path of the electrolysis cell at 10 sccm, an aqueous potassium hydroxide solution (concentration 1 M KOH) was introduced into the anode solution flow path at a flow rate of 20 mL/min. Next, the voltage of 2.2 V was applied between the anode and the cathode to make the current flow by controlling the voltage with the use of the power controller, the $CO_2$ electrolytic reaction was caused, and a cell voltage at that time was measured and collected by the electrolytic regulator 502. Further, a part of gas output from the $CO_2$ gas flow path was collected, and production amounts of CO gas produced by the reduction reaction of $CO_2$ and $H_2$ gas produced by the reduction reaction of water were analyzed by a gas chromatograph. The electrolytic regulator 502 calculated and collected a partial current density of CO or $H_2$ and Faradaic efficiency being a ratio between a total current density and the partial current density, based on the gas production amounts. A total current value at this time was 600 mA. Table 1 lists the results (initial data).

From the result of the gas chromatograph, the Faradaic efficiency of hydrogen was initially 3.1% and that of CO was 97.6%. A total gas flow rate measured by using a piston-type flow rate sensor at this time was 10.13 ccm. It was thereby predicted that a flow rate of hydrogen was 0.130 ccm, and a flow rate of CO was 4.078 ccm. At this time, a potential difference from a reference electrode (Ag/AgCl) provided at the anode solution flow path 12 was 0.61 V regarding the anode and −1.2 V regarding the cathode. A cell voltage at that time was 2.2 V.

As a result of low current operation at 600 mA so as not to largely change a produced gas amount, the cell voltage became 2.25 V after one hour had passed. The potential difference from the reference electrode (Ag/AgCl) at this time was 0.64 V regarding the anode, and −1.3 V regarding the cathode. The total gas flow rate measured by using the piston type flow rate sensor was 10.15 ccm. Table 1 lists the results (actual-measurement data).

In reference data (Reference data 1 to 3) acquired previously after one hour had passed since the operation was started, it was predicted that the flow rate of hydrogen was 0.150 ccm and the flow rate of CO was 4.036 ccm because a ratio of production amounts between hydrogen and CO at a total gas flow rate of 10.15 ccm was 3.6% for hydrogen and 96.6% for CO when the cell voltage was 2.25 V. From the result of the gas chromatograph, hydrogen was 3.6%, CO was 96.4%, and it was calculated that the flow rate of hydrogen was 0.150 ccm and the flow rate of CO was 4.027 ccm, and difference between both was small. Reference data of the flow rate of hydrogen and the flow rate of CO in each of cases when the cell voltages were 2.25 V, 2.23 V, 2.27 V acquired previously after one hour had passed since the operation was started are listed in Table 1. Note that mole listed in Table 1 corresponds to a generation amount of a reduction product, and a coulomb amount indicates an electric charge amount (electric charges carried by a current of 1 A for one second) in accordance with the generation amount.

It can be seen that the production amount of CO is larger when it is operated at 2.23 V. In addition, it is effective for improvement in electrolysis efficiency because the voltage decreases, and a large amount of CO gas can be obtained with a little energy amount. The electrolysis conditions of the electrolytic device can be set by predicting the gas flow rate.

flow rate sensors based on the above value. It is possible to calculate the gas flow rate through these operations and to give feedback to enable an optimum operation of the cell.

TABLE 1

|  | Initial | One hour later | | | |
|---|---|---|---|---|---|
|  |  | Actual measurement | Reference 1 | Reference 2 | Reference 3 |
| Total current | 600 mA | 600 mA | 600 mA | 600 mA | 600 mA |
| Introduced $CO_2$ flow rate | 10 sccm | 10 sccm | 10 sccm | 10 sccm | 10 sccm |
| Cell voltage | 2.2 V | 2.25 V | 2.25 V | 2.23 V | 2.27 V |
| Anode potential (Ag/AgCl) | 0.61 V | 0.64 V | 0.61 V | 0.61 V | 0.61 V |
| Cathode potential (Ag/AgCl) | −1.2 V | −1.3 V | −1.3 V | −1.3 V | −1.3 V |
| Coulomb amount | 36 c | 36 c | 36 c | 35.58 c | 37.5 |
| Mole | 0.37 mmol | 0.37 mmol | 0.37 mmol | 0.37 mmol | 0.37 mmol |
| Faradaic efficiency of CO (%) | 97.6% | 96.4% | 96.6% | 97.3% | 95.2% |
| Faradaic efficiency of $H_2$ (%) | 3.1% | 3.6% | 3.6% | 3.2% | 3.8% |
| Flow rate (TOTAL) | 10.12 ccm | 10.15 ccm | 10.15 ccm | 10.13 ccm | 10.16 ccm |
| Flow rate ($CO_2$) | 5.92 ccm | 5.97 ccm | 5.96 ccm | 5.98 ccm | 5.85 ccm |
| Flow rate (CO) | 4.07 ccm | 4.02 ccm | 4.03 ccm | 4.01 ccm | 4.14 ccm |
| Flow rate ($H_2$) | 0.129 ccm | 0.150 ccm | 0.150 ccm | 0.132 ccm | 0.165 ccm |

Comparative Example 1

The electrolytic device was operated similarly to Example 1. The cell voltage was set as 2.27 V to try to increase the CO production amount by increasing the current value in order to operate to correspond to lowering of performance mainly due to the increase of the cell voltage after one hour had passed since the operation was started. As a result of actual measurement by the gas chromatograph, the Faradaic efficiencies were 95.2% (CO), 3.8% ($H_2$), the actual CO flow rate was 3.92 ccm, and the CO production amount decreased. The electrolysis efficiency decreased due to the effect of the increased cell voltage.

Example 2

The electrolytic device was operated similarly to Example 1 except that a piston-type volume flow rate sensor and a differential-pressure type flow rate sensor using orifice were set at a cathode product discharge gas flow path. A total flow rate at a flow path outlet when the operation was started was 10.13 ccm by the piston type volume flow rate sensor, and 9.29 ccm by the differential-pressure type flow rate sensor. At this time, the CO flow rate was calculated to be 4.0783 ccm by calculating a gas density ratio between CO and hydrogen from the difference of both flow rate sensors. It is possible to predict the gas flow rate through these operations and to give feedback to enable an optimum operation of the electrolysis cell 2.

Example 3

The electrolytic device was operated similarly to Example 2 except that the cell voltage was set as 2.3 V. A total flow rate at the flow path outlet when the operation was started was 10.13 ccm by the piston type volume flow rate sensor, and 9.04 ccm by the differential-pressure type flow rate sensor. In Reference data 2 at the same cell voltage, the Faradaic efficiency was 98% from the voltage and the pH value of the electrolytic solution. The calculation was therefore made while setting the Faradaic efficiency as 98. It was calculated that 0.2955 mmol of hydrogen and CO were produced as a total for one minute. The CO flow rate was calculated to be 5.320 ccm by using the gas density ratio between CO and hydrogen from the difference between both Example 4

The electrolytic device similar to Example 1 was used, and cathode outlet gas was supplied to a methanol reactor with a diaphragm pump while setting a flow rate at 10.15 ccm. A reactor was a fixed-bed flow type reactor, glass wool was filled into a ½ inch SUS pipe, and 1.0 g of Pd/ZnO powder was used as a catalyst. Aluminum blocks were provided so as to sandwich the SUS pipe, and the SUS pipe was heated to 215° C. by cartridge heaters provided at the upside and downside. A valve to adjust the pressure was provided at the outlet.

In Reference data 1, since the CO flow rate is 4.03 ccm, the flow rate of hydrogen required for methanol synthesis is 8.06 ccm. The flow rate of hydrogen of 0.15 ccm contained in the cathode gas was subtracted from 8.06 ccm, and CO was mixed with the hydrogen gas at the flow rate of 7.91 ccm to be supplied to the reactor together with the cathode outlet gas. Gas at a reactor outlet was ice-cooled to collect methanol. One hour later, 0.345 g of methanol was obtained.

Comparative Example 2

A methanol synthesis reaction was carried out similarly to Example 4 by using the gas from the cathode outlet of the electrolysis cell similar to Comparative example 1. A predetermined operation was performed while supplying gas from the diaphragm pump at the cathode outlet to the reactor at the flow rate of 10 ccm. As a result, it was verified that the cell voltage was unstable and the cell voltage was increased. In addition, the cell pressure varied to cause unstable operation. When the methanol synthesis was performed with the same reactor as Example 4 while setting the cathode outlet gas as 8 ccm, 0.32 g of methanol was obtained. It can be seen that a methanol synthesis amount decreases because the prediction of the flow rate of the carbon compound is not performed.

Example 5

The electrolytic device similar to Example 1 was used, the flow rate of the cathode outlet gas was set as 10.15 ccm, and cathode outlet gas was supplied to the methanol reactor with the diaphragm pump similarly to Example 4. A CO concentration of the outlet gas was measured by using an infrared absorption spectrum at a wavelength region of 2 to 5 µm. Concretely, the concentration was found from an absorption wavelength of 2360 cm$^{-1}$. Similarly, a concentration of CO$^2$ can be found also from 660 cm$^1$. The CO flow rate was predicted to be 4.05 ccm from the data.

Since an average of the CO flow rates of the reference data is about 4.05 ccm, the hydrogen flow rate required for the methanol synthesis is 8.10 ccm. The hydrogen flow rate of 0.15 ccm contained in the cathode gas was subtracted from 8.10 ccm, and CO was mixed with the hydrogen gas at the flow rate of 7.95 ccm to be supplied to the reactor together with the cathode outlet gas. The gas at the reactor outlet was ice-cooled to collect methanol. One hour later, 0.343 g of methanol was obtained. It can be seen that the methanol production amount becomes large compared to Example 2 where the CO sensor using the infrared absorption was not used.

Note that configurations of the above-described embodiments may be each applied in combination, and further may be partially substituted. While certain embodiments of the invention have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the invention.

What is claimed is:

1. A carbon dioxide reduction system, comprising:
an electrolytic unit including
an electrolysis cell having a cathode to reduce a first substance containing carbon dioxide and thus produce a first product containing a carbon compound, and an anode to oxidize a second substance containing water or hydroxide ions and thus produce a second product containing oxygen,
a detection unit to acquire data defining operation states of the electrolysis cell, and
an electrolytic regulator to regulate electrolysis conditions of the electrolysis cell;
a compression unit including
a compressor to compress the first product, and
a compressor regulator to regulate compression conditions of the first product by the compressor; and
a controller programmed to predict a flow rate of the carbon compound discharged from the electrolysis cell in accordance with the data to control regulation of the compression conditions in accordance with the predicted flow rate, wherein
the first substance further contains water,
the first product further contains hydrogen,
the detection unit includes:
a first flow rate sensor to measure a flow rate of the first product discharged from the electrolysis cell by a first measurement method to acquire a first flow rate data; and
a second flow rate sensor to measure a flow rate of the first product by a second measurement method to acquires a second flow rate data, and
the controller is programmed to predict a flow rate of the carbon compound and a flow rate of hydrogen discharged from the electrolysis cell in accordance with a plurality of data having the first flow rate data and the second flow rate data, and control regulation of the compression conditions in accordance with the predicted flow rate.

2. The system according to claim 1, wherein
the first measurement method is an actual-measurement method, and
the second measurement method is an inferential method.

3. The system according to claim 1, wherein
the controller is programmed to control regulation of the electrolysis conditions in accordance with the predicted flow rate.

4. The system according to claim 3, further comprising:
an analysis unit to analyze data indicating operation states of the electrolysis cell, wherein
the controller is programmed to control regulation of the electrolysis conditions in accordance with the analyzed data.

5. A carbon dioxide reduction system, comprising:
an electrolytic unit including
an electrolysis cell having a cathode to reduce a first substance containing carbon dioxide and thus produce a first product containing a carbon compound, and an anode to oxidize a second substance containing water or hydroxide ions and thus produce a second product containing oxygen,
a detection unit to acquire data defining operation states of the electrolysis cell, and
an electrolytic regulator to regulate electrolysis conditions of the electrolysis cell;
a compression unit including
a compressor to compress the first product, and
a compressor regulator to regulate compression conditions of the first product by the compressor; and
a controller programmed to predict a flow rate of the carbon compound discharged from the electrolysis cell in accordance with the data to control regulation of the compression conditions in accordance with the predicted flow rate, wherein
the detection unit includes an optical sensor to measure spectrum of the first product in a cathode solution flow path and thus acquire spectral data, and
the controller is programmed to predict a flow rate of the carbon compound discharged from the electrolysis cell in accordance with a plurality of data containing the spectral data, and control regulation of the compression conditions in accordance with the predicted flow rate.

6. The system according to claim 5, wherein
the first substance further contains water,
the first product further contains hydrogen,
the detection unit includes:
a first flow rate sensor to measure a flow rate of the first product discharged from the electrolysis cell by a first measurement method to acquire a first flow rate data; and
a second flow rate sensor to measure a flow rate of the first product by a second measurement method to acquires a second flow rate data, and
the controller is programmed to predict a flow rate of the carbon compound and a flow rate of hydrogen discharged from the electrolysis cell in accordance with a plurality of data containing the spectral data, the first flow rate data, and the second flow rate data, and control regulation of the compression conditions in accordance with the predicted flow rate.

7. The system according to claim 5, wherein
the electrolysis cell further includes a gas flow path through which carbon dioxide supplied to the cathode flows, and a solution flow path to supply an electrolytic solution containing water and being supplied to at least one selected from the group consisting of the cathode and the anode, and the plurality of data further has data indicating at least one parameter selected from the group consisting of a voltage between the cathode and the anode, a potential of the cathode, a potential of the anode, a pressure in the solution flow path, a temperature of the electrolytic solution, pH of the electrolytic solution, an operating time of the electrolysis cell, the number of starts of the electrolysis cell, and the number of stops of the electrolysis cell.

8. The system according to claim 7, wherein the compressor has a tank to accommodate the compressed first product, and the plurality of data further has data indicating a temperature in the tank and data indicating a pressure in the tank.

9. The system according to claim 7, wherein the plurality of data further has data indicating at least one parameter selected from the group consisting of an electric power amount supplied from a power storage device to the electrolysis cell, at least a part of a power demand amount of the carbon dioxide reduction system, an electric energy amount supplied from a renewable energy source to the electrolysis cell, a flow rate of the carbon dioxide supplied from a carbon dioxide source to the electrolysis cell, and an operating state of a plant.

10. The system according to claim 5, wherein the controller is programmed to control regulation of the electrolysis conditions in accordance with the predicted flow rate.

11. The system according to claim 10, further comprising:

an analysis unit to analyze data indicating operation states of the electrolysis cell, wherein the controller is programmed to control regulation of the electrolysis conditions in accordance with the analyzed data.

* * * * *